(12) United States Patent
Karube

(10) Patent No.: US 12,268,553 B2
(45) Date of Patent: Apr. 8, 2025

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Mikihiko Karube, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 141 days.

(21) Appl. No.: 18/160,942

(22) Filed: Jan. 27, 2023

(65) Prior Publication Data
US 2023/0165563 A1 Jun. 1, 2023

Related U.S. Application Data

(63) Continuation of application No. PCT/JP2021/011369, filed on Mar. 19, 2021.

(30) Foreign Application Priority Data

Aug. 27, 2020 (JP) ................................ 2020-143290

(51) Int. Cl.
A61B 8/00 (2006.01)
(52) U.S. Cl.
CPC ............ A61B 8/4254 (2013.01); A61B 8/461 (2013.01); A61B 8/469 (2013.01)
(58) Field of Classification Search
CPC ........ A61B 8/4254; A61B 8/461; A61B 8/469
See application file for complete search history.

(56) References Cited

U.S. PATENT DOCUMENTS

2012/0007863 A1 1/2012 Endo et al.
2014/0194722 A1 7/2014 Lee et al.
(Continued)

FOREIGN PATENT DOCUMENTS

JP 2009-225905 A 10/2009
JP 2010-233961 A 10/2010
(Continued)

OTHER PUBLICATIONS

International Search Report issued in PCT/JP2021/011369; mailed Jun. 1, 2021.
(Continued)

*Primary Examiner* — Dixomara Vargas
(74) *Attorney, Agent, or Firm* — Studebaker Brackett PLLC

(57) ABSTRACT

An ultrasound diagnostic apparatus (1) includes an ultrasound probe (2); an image generation unit (22) that generates an ultrasound image; a monitor (24); a position sensor (14) that acquires positional information of the ultrasound probe (2); a scanning direction instruction unit (15) for instructing a user on a direction to perform the scan by the ultrasound probe (2); a boundary recognition unit (27) that recognizes a boundary between a normal portion and an abnormal portion of a subject by analyzing the ultrasound image; and an instruction control unit (28) that specifies the direction to perform the scan by the ultrasound probe (2) on the basis of the positional information of the ultrasound probe (2) acquired by the position sensor (14) and the boundary recognized by the boundary recognition unit (27), and instructs the user on the specified direction to perform the scan by using the scanning direction instruction unit (15).

12 Claims, 13 Drawing Sheets

(56) References Cited

U.S. PATENT DOCUMENTS

2016/0000411 A1* 1/2016 Raju ............... A61B 5/6842
 600/443
2017/0181726 A1 6/2017 Schneider et al.

FOREIGN PATENT DOCUMENTS

| JP | 2013-158361 A | 8/2013 |
| JP | 2014-133133 A | 7/2014 |
| JP | 2014-138638 A | 7/2014 |
| JP | 2017-509417 A | 4/2017 |

OTHER PUBLICATIONS

International Preliminary Report On Patentability and Written Opinion issued in PCT/JP2021/011369; issued Feb. 28, 2023.
An Office Action; "Notice of Reasons for Refusal," mailed by the Japanese Patent Office on Nov. 14, 2023, which corresponds to Japanese Patent Application No. 2022-545293 and is related to U.S. Appl. No. 18/160,942; with English language translation.

* cited by examiner

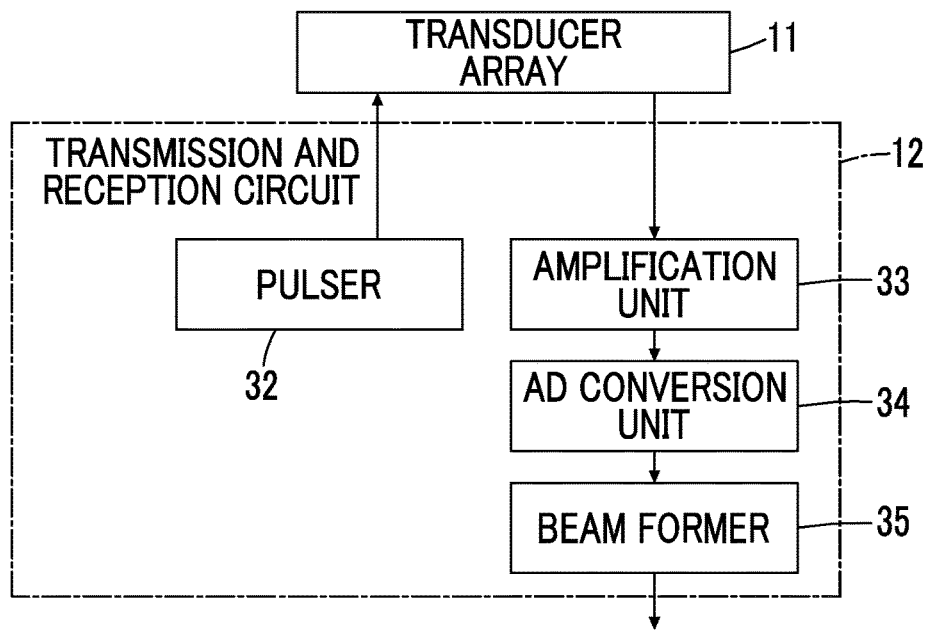
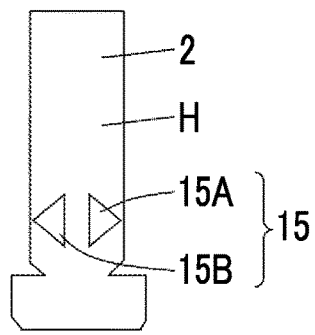
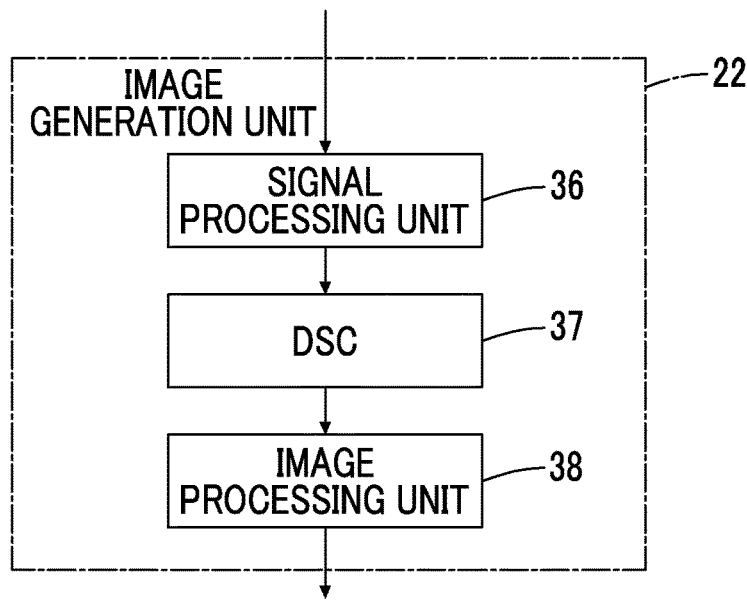

M2　　　U　　　24　　　M1

ULTRASOUND DIAGNOSTIC APPARATUS AND CONTROL METHOD OF ULTRASOUND DIAGNOSTIC APPARATUS

CROSS-REFERENCE TO RELATED APPLICATIONS

This application is a Continuation of PCT International Application No. PCT/JP2021/011369 filed on Mar. 19, 2021, which claims priority under 35 U.S.C. § 119(a) to Japanese Patent Application No. 2020-143290 filed on Aug. 27, 2020. The above applications are hereby expressly incorporated by reference, in its entirety, into the present application.

BACKGROUND OF THE INVENTION

1. Field of the Invention

The present invention relates to an ultrasound diagnostic apparatus, and a control method of the ultrasound diagnostic apparatus which are for observing an abnormal portion of a subject.

2. Description of the Related Art

In the related art, an ultrasound diagnostic apparatus that can assist a user in the ultrasound diagnosis has been developed. For example, JP2009-225905A discloses an ultrasound diagnostic apparatus which assists the user in the ultrasound diagnosis by storing positional information of a region where a scan has been performed by an ultrasound probe, in a site of a subject, and displaying a region that has not been examined.

SUMMARY OF THE INVENTION

The ultrasound diagnostic apparatus is sometimes used to perform an examination for an abnormal portion such as pressure ulcers, and edema that is a kind of phlebitis occurring in the subject. Since such an abnormal portion generally spreads three-dimensionally in the subject, it is difficult for the user to determine how far the abnormal portion spreads at a glance. Therefore, for example, even using a technique disclosed in JP2009-225905A, it is difficult to grasp a boundary between the abnormal portion and a normal portion so that in some cases, the examination of the abnormal portion is not sufficiently and efficiently performed, for example, a region that has been scanned already is repeatedly scanned, all aver the region where the abnormal portion has spread cannot be scanned, not only the abnormal portion but also the normal portion is carefully scanned, and the like.

The present invention has been made in order to solve such a problem in the related art, and an object of the present invention is to provide an ultrasound diagnostic apparatus and a control method of the ultrasound diagnostic apparatus which can sufficiently and efficiently examine an abnormal portion.

In order to achieve the object, an ultrasound diagnostic apparatus according to an aspect of the present invention includes an ultrasound probe; an image generation unit that generates an ultrasound image by performing a scan of an ultrasound beam on an abnormal portion of a subject by using the ultrasound probe; a monitor that displays the ultrasound image; a position sensor that is attached to the ultrasound probe, and acquires positional information of the ultrasound probe; a scanning direction instruction unit for instructing a user on a direction to perform the scan by the ultrasound probe; a boundary recognition unit that recognizes a boundary between a normal portion and the abnormal portion of the subject by analyzing the ultrasound image; and an instruction control unit that specifies the direction to perform the scan by the ultrasound probe on the basis of the positional information of the ultrasound probe acquired by the position sensor and the boundary recognized by the boundary recognition unit, and instructs the user on the specified direction to perform the scan by using the scanning direction instruction unit.

The scanning direction instruction unit can be formed by an LED lamp attached to the ultrasound probe, and the instruction control unit can instruct the direction to perform the scan by using a color of light emitted from the LED lamp or blinking the LED lamp.

Alternatively, the scanning direction instruction unit can be formed by the monitor, and the instruction control unit can display the direction to perform the scan on the monitor.

Alternatively, the ultrasound probe can include a vibration mechanism, the scanning direction instruction unit can be formed by the vibration mechanism, and the instruction control unit can instruct the direction to perform the scan according to a vibration pattern of the vibration mechanism.

The ultrasound diagnostic apparatus can further include a tablet terminal connected to the ultrasound probe, the tablet terminal can include a vibration mechanism, the scanning direction instruction unit can be formed by the vibration mechanism, and the instruction control unit can instruct the direction to perform the scan according to a vibration pattern of the vibration mechanism.

The instruction control unit can specify a scanning direction that reduces overlapping with a scanned region on the basis of the positional information of the ultrasound probe acquired by the position sensor.

In a case where a gap is generated between the ultrasound probe and a scanned region, the instruction control unit can specify a scanning direction to approach the scanned region on the basis of the positional information of the ultrasound probe acquired by the position sensor.

The instruction control unit can specify a scanning direction passing through the boundary recognized by the boundary recognition unit on the basis of the positional information of the ultrasound probe acquired by the position sensor.

The ultrasound diagnostic apparatus can further include a non-depicted portion extraction unit that identifies a portion which is not depicted in the ultrasound image due to separation of the ultrasound probe from a body surface of the subject, on the basis of the ultrasound image and the positional information of the ultrasound probe, and displays the portion on the monitor.

In a case where the ultrasound probe performs the scan on the abnormal portion in one direction of two directions orthogonal to each other and boundaries on both sides of the abnormal portion are recognized by the boundary recognition unit, the instruction control unit can instruct the user to shift to the scan in the other direction of the two directions by using the scanning direction instruction unit.

The instruction control unit can estimate a remaining boundary between the normal portion and the abnormal portion of the subject on the basis of the boundary recognized by the boundary recognition unit, and specify the direction to perform the scan on the basis of the estimated remaining boundary.

The ultrasound diagnostic apparatus can further include a memory that stores the ultrasound image and the positional information of the ultrasound probe acquired by the position sensor in association with each other; and a trajectory calculation unit that calculates a trajectory of the scan of the ultrasound probe, and displays the trajectory on the monitor, and in this case, in a case where any position on the trajectory displayed on the monitor is designated by the user, the ultrasound image corresponding to the any position can be read out from the memory, and be displayed on the monitor.

A control method of an ultrasound diagnostic apparatus according to an aspect of the present invention includes generating an ultrasound image by performing a scan of an ultrasound beam on an abnormal portion of a subject by using an ultrasound probe; acquiring positional information of the ultrasound probe by using a position sensor attached to the ultrasound probe; recognizing a boundary between a normal portion and the abnormal portion of the subject by analyzing the ultrasound image; and specifying a direction to perform the scan by the ultrasound probe on the basis of the acquired positional information of the ultrasound probe and the recognized boundary, and instructing the user on the specified direction to perform the scan.

According to the present invention, the ultrasound diagnostic apparatus includes a position sensor that is attached to the ultrasound probe and acquires positional information of the ultrasound probe; a scanning direction instruction unit for instructing a user on a direction to perform the scan by the ultrasound probe; a boundary recognition unit that recognizes a boundary between a normal portion and an abnormal portion of a subject by analyzing the ultrasound image; and an instruction control unit that specifies the direction to perform the scan by the ultrasound probe on the basis of the positional information of the ultrasound probe acquired by the position sensor and the boundary recognized by the boundary recognition unit, and instructs the user on the specified direction to perform the scan by using the scanning direction instruction unit. Therefore, it is possible to sufficiently and efficiently examine the abnormal portion.

BRIEF DESCRIPTION OF THE DRAWINGS

FIG. 2 is a block diagram illustrating an internal configuration of a transmission and reception circuit in the first embodiment of the present invention.

FIG. 3 is a diagram schematically illustrating an example of an LED lamp of an ultrasound probe in the first embodiment.

FIG. 4 is a block diagram illustrating an internal configuration of an image generation unit in the first embodiment of the present invention.

DESCRIPTION OF THE PREFERRED EMBODIMENTS

Hereinafter, embodiments of the invention will be described with reference to the accompanying drawings.

The description of configuration requirements described below is given on the basis of the representative embodiment of the present invention, but the present invention is not limited to such an embodiment.

In the present specification, a numerical range represented using "to" means a range including the numerical values before and after "to" as a lower limit value and an upper limit value.

In the present specification, the terms "same" and "identical" include an error range generally allowed in the technical field.

First Embodiment

Figure 1:
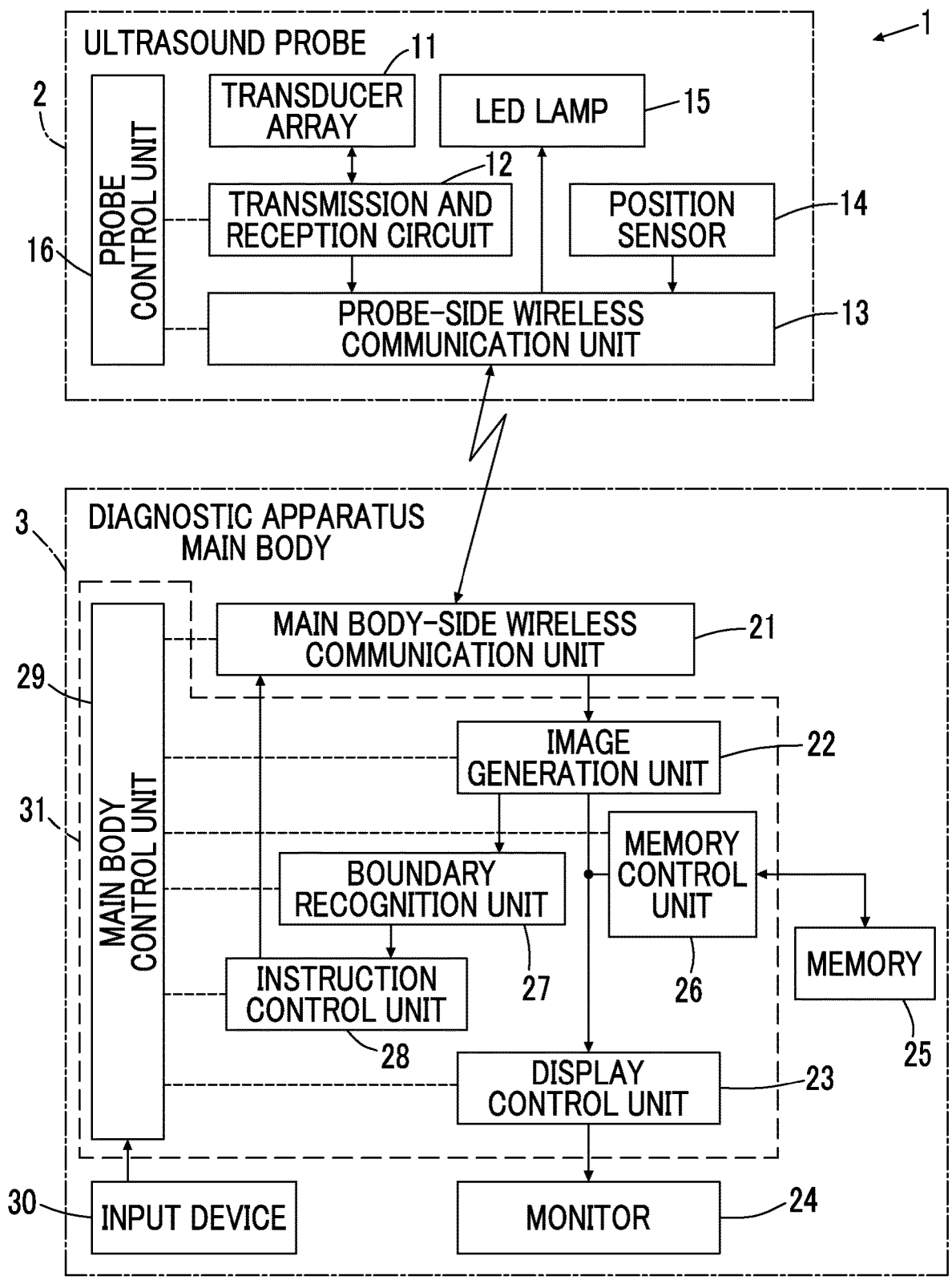
FIG. 1 is a block diagram illustrating a configuration of an ultrasound diagnostic apparatus according to a first embodiment of the present invention.

FIG. 1 illustrates a configuration of an ultrasound diagnostic apparatus 1 according to a first embodiment of the present invention. The ultrasound diagnostic apparatus 1 includes an ultrasound probe 2 and a diagnostic apparatus main body 3. The ultrasound probe 2 and the diagnostic apparatus main body 3 are connected to each other by wireless communication.

The ultrasound probe 2 has a transducer array 11, and a transmission and reception circuit 12 and a probe-side wireless communication unit 13 are sequentially connected to the transducer array 11. A position sensor 14 and a light emitting diode (LED) lamp 15 are attached to the ultrasound probe 2, and each of the position sensor 14 and the LED lamp 15 is connected to the probe-side wireless communication unit 13. The transmission and reception circuit 12 and the probe-side wireless communication unit 13 are connected to a probe control unit 16.

The diagnostic apparatus main body 3 includes a main body-side wireless communication unit 21, and an image generation unit 22, a display control unit 23, and a monitor 24 are sequentially connected to the main body-side wireless communication unit 21. The diagnostic apparatus main body 3 includes a memory 25, and a memory control unit 26 is connected to the memory 25. The memory control unit 26 is connected to the image generation unit 22 and the display control unit 23. A boundary recognition unit 27 is connected to the image generation unit 22, and an instruction control unit 28 is connected to the boundary recognition unit 27. The instruction control unit 28 is connected to the main body-side wireless communication unit 21.

A main body control unit 29 is connected to the main body-side wireless communication unit 21, the image generation unit 22, the display control unit 23, the memory control unit 26, the boundary recognition unit 27, and the instruction control unit 28. An input device 30 is connected to the main body control unit 29.

The image generation unit 22, the display control unit 23, the memory control unit 26, the boundary recognition unit 27, the instruction control unit 28, and the main body control unit 29 constitute a main body-side processor 31.

The transducer array 11 of the ultrasound probe 2 illustrated in FIG. 1 has a plurality of transducers arranged in a one-dimensional or two-dimensional manner. According to a drive signal supplied from the transmission and reception circuit 12, each of the transducers transmits an ultrasonic wave and receives an ultrasound echo from a subject to output a signal based on the ultrasound echo. For example, each transducer is configured by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The transmission and reception circuit 12 causes the transducer array 11 to transmit the ultrasonic wave and generates a sound ray signal on the basis of a reception signal acquired by the transducer array 11, under the control of the probe control unit 16. As illustrated in FIG. 2, the transmission and reception circuit 12 has a pulser 32 connected to the transducer array 11, and an amplification unit 33, an analog digital (AD) conversion unit 34, and a beam former 35 that are sequentially connected in series from the transducer array 11.

The pulser 32 includes, for example, a plurality of pulse generators, and the pulser 32 adjusts the amount of delay of each drive signal so that ultrasonic waves transmitted from the plurality of transducers of the transducer array 11 form an ultrasound beam on the basis of a transmission delay pattern selected according to the control signal from the probe control unit 16, and supplies the obtained signals to the plurality of transducers. Thus, in a case where a pulsed or continuous-wave voltage is applied to the electrodes of the transducers of the transducer array 11, the piezoelectric body expands and contracts to generate pulsed or continuous-wave ultrasonic waves from each transducer. From the combined wave of these ultrasonic waves, an ultrasound beam is formed.

The transmitted ultrasound beam is reflected by a target, for example, a site of the subject, and propagates toward the transducer array 11 of the ultrasound probe 2. The ultrasound echo propagating toward the transducer array 11 in this manner is received by each transducer constituting the transducer array 11. In this case, each transducer constituting the transducer array 11 expands and contracts by receiving the propagating ultrasound echo to generate a reception signal that is an electric signal, and outputs the reception signal to the amplification unit 33.

The amplification unit 33 amplifies the signals input from each transducer constituting the transducer array 11, and transmits the amplified signals to the AD conversion unit 34. The AD conversion unit 34 converts the signal transmitted from the amplification unit 33 into digital reception data, and transmits the reception data to the beam former 35. The beam former 35 performs so-called reception focusing processing in which addition is performed by giving delays to respective pieces of the reception data converted by the AD conversion unit 34 according to a sound speed distribution or a sound speed set on the basis of a reception delay pattern selected according to the control signal from the probe control unit 16. Through the reception focusing processing, a sound ray signal in which each piece of the reception data converted by the AD conversion unit 34 is phased and added and the focus of the ultrasound echo is narrowed is acquired.

The probe-side wireless communication unit 13 is configured by a circuit or the like including an antenna for transmitting and receiving radio waves, and performs wireless communication with the main body-side wireless communication unit 21 of the diagnostic apparatus main body 3 under the control of the probe control unit 16. The probe-side wireless communication unit 13 modulates a carrier on the basis of the sound ray signal generated by the transmission and reception circuit 12, generates a transmission signal representing the sound ray signal, and wirelessly transmits the generated transmission signal to the main body-side wireless communication unit 21 of the diagnostic apparatus main body 3. Similarly, the probe-side wireless communication unit 13 also generates the transmission signal for positional information of the ultrasound probe 2 acquired by the position sensor 14, and wirelessly transmits the generated transmission signal to the main body-side wireless communication unit 21.

As the modulation method of the carrier, for example, amplitude shift keying (ASK), phase shift keying (PSK), quadrature phase shift keying (QPSK), 16 quadrature amplitude modulation (16 QAM), or the like is used.

The position sensor 14 is a sensor for detecting the positional information of the ultrasound probe 2. The position sensor 14 is configured by, for example, an acceleration sensor, a gyro sensor, and a magnetic sensor.

The LED lamp 15 is attached to the ultrasound probe 2 to be visible to the user, and is used as a scanning direction instruction unit for instructing the user on a direction to perform the scan by the ultrasound probe 2. For example, as illustrated in FIG. 3, the LED lamp 15 is configured by a right lamp 15A and a left lamp 15B, and both the right lamp 15A and the left lamp 15B are arranged such that light emitting portions are positioned outside a housing H of the ultrasound probe 2. In this case, for example, by turning on the right lamp 15A or the left lamp 15B, an instruction to move the ultrasound probe 2 to the right lamp 15A side or an instruction to move the ultrasound probe 2 to the left lamp 15B side can be made.

The probe control unit 16 controls each unit of the ultrasound probe 2 on the basis of a program and the like stored in advance.

Although not illustrated, a battery that supplies power to each unit of the ultrasound probe 2 is built in the ultrasound probe 2.

Similarly to the probe-side wireless communication unit 13, the main body-side wireless communication unit 21 of the diagnostic apparatus main body 3 is configured by a circuit or the like including an antenna for transmitting and receiving radio waves, and performs wireless communication with the probe-side wireless communication unit 13 of the ultrasound probe 2 under the control of the main body control unit 29. In this case, the main body-side wireless communication unit 21 demodulates the transmission signal wirelessly transmitted from the probe-side wireless communication unit 13 to obtain sound ray signal and the positional information of the ultrasound probe 2. The main body-side wireless communication unit 21 sends the obtained sound ray signal to the image generation unit 22, and sends the obtained positional information of the ultrasound probe 2 to the memory 25 via the image generation unit 22 and the memory control unit 26.

The main body-side wireless communication unit 21 modulates the carrier on the basis of the instruction information sent from the instruction control unit 28, generates a transmission signal representing the instruction information, and wirelessly transmits the generated transmission signal to the probe-side wireless communication unit 13. Similarly to the modulation method used in the probe-side wireless communication unit 13, as the modulation method of the carrier, ASK, PSK, QPSK, 16 QAM, or the like is used.

As illustrated in FIG. 4, the image generation unit 22 has a configuration in which a signal processing unit 36, a digital scan converter (DSC) 37, and an image processing unit 38 are sequentially connected in series.

The signal processing unit 36 generates a B-mode image signal which is tomographic image information regarding tissues inside the subject, by performing, on the sound ray signal sent from the main body-side wireless communication unit 21, correction of the attenuation due to the distance according to the depth of the reflection position of the ultrasonic wave and then performing envelope detection processing.

The DSC 37 converts (raster conversion) the B-mode image signal generated by the signal processing unit 36 into an image signal according to a normal television signal scanning method.

The image processing unit 38 performs various kinds of necessary image processing such as gradation processing on the B-mode image signal input from the DSC 37, and then sends the B-mode image signal to the display control unit 23 and to the memory 25 via the memory control unit 26. In the following, the B-mode image signal subjected to the image processing by the image processing unit 38 is simply referred to as an ultrasound image.

The memory 25 is a memory that stores ultrasound images of the series of a plurality of frames, which are generated for each diagnosis by the image generation unit 22, and the positional information of the ultrasound probe 2. Here, as the memory 25, recording media such as a flash memory, a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), a server, or the like can be used.

The memory control unit 26 controls the storage and reading out of the data in the memory 25. Specifically, the memory control unit 26 stores the ultrasound image generated by the image generation unit 22 and the positional information of the ultrasound probe 2 in a case where the ultrasound image is captured, in the memory 25 in association with each other. Further, the memory control unit 26 reads out the ultrasound image and the positional information of the ultrasound probe 2, which are stored in the memory 25, according to the instruction of the main body control unit 29, and sends the read out ultrasound image and positional information to the display control unit 23 or to the boundary recognition unit 27 via the image generation unit 22.

In a case where the ultrasound image of a tomographic plane including the abnormal portion is generated by the image generation unit 22, the boundary recognition unit 27 recognizes the boundary between the normal portion of the subject and the abnormal portion of the subject by analyzing the ultrasound image. Here, the abnormal portion in the present invention refers to, for example, a site where a so-called pressure ulcer has occurred, a site where edema has occurred in the vicinity of the pressure ulcer, a site where edema which is a kind of phlebitis, and surrounding regions thereof.

Figure 5:
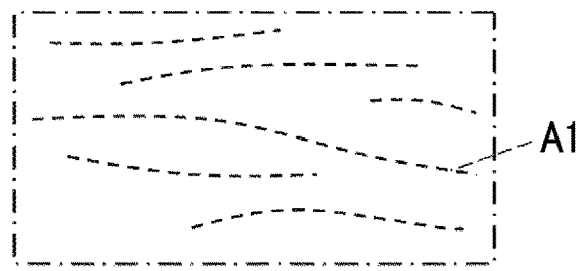
FIG. 5 is a diagram schematically illustrating an unclear layered structure.
Figure 6:
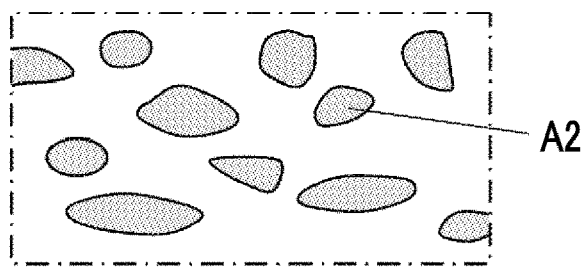
FIG. 6 is a diagram schematically illustrating a Cobblestone-like pattern.
Figure 7:
FIG. 7 is a diagram schematically illustrating a Cloud-like pattern.
Figure 8:
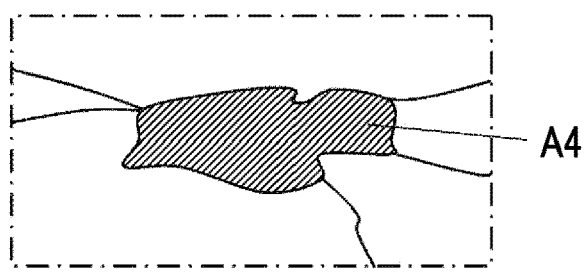
FIG. 8 is a diagram schematically illustrating a pattern in which fluid retention is observed.

Examples of a structure representing the abnormal portion in the ultrasound image include, for example, an unclear layered structure A1 illustrated in FIG. 5, a Cobblestone-like pattern A2 illustrated in FIG. 6, a Cloud-like pattern A3 illustrated in FIG. 7, and a pattern A4 in which the brightness is low and fluid retention is observed as illustrated in FIG. 8. The unclear layered structure A1 illustrated in FIG. 5 corresponds to weak edema, the Cobblestone-like pattern A2 illustrated in FIG. 6 corresponds to strong edema, the Cloud-like pattern A3 illustrated in FIG. 7 corresponds to suspected necrosis, and the pattern A4 in which fluid retention is observed illustrated in FIG. 8 corresponds to suspected abscess, hematoma, or dropsy.

The boundary recognition unit 27 recognizes a region in which, for example, the structures as illustrated in FIGS. 5 to 8 as the abnormal portion of the subject, and recognizes the boundary between the normal portion and the abnormal portion. As the recognition method for the normal portion and the abnormal portion, for example, the boundary recognition unit 27 can use a deep learning method such as so-called U-Net, a so-called template matching method, a machine learning method using a support vector machine (SVM), AdaBoost, and the like, a machine learning method described in Csurka et al.: Visual Categorization with Bags of Keypoints, Proc. of ECCV Workshop on Statistical Learning in Computer Vision, pp. 59-74 (2004), and the like.

Figure 9:
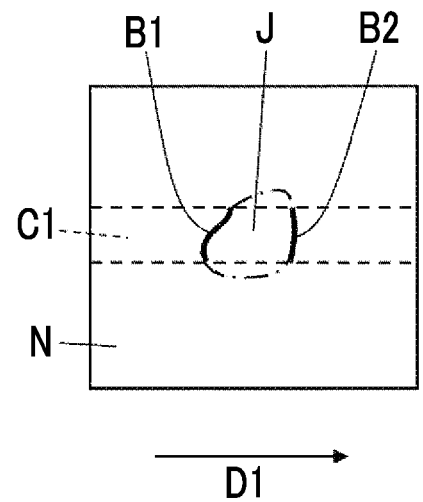
FIG. 9 is a diagram schematically illustrating a trajectory of one scan of the ultrasound probe with respect to an abnormal portion.

For example, in a case where the ultrasound probe 2 performs a scan to traverse an abnormal portion J along a first direction D1 as in a trajectory C1 indicated by a dotted line region in FIG. 9, the boundary recognition unit 27 recognizes boundaries B1 and B2 between the abnormal portion J and a normal portion N by analyzing the ultrasound images of the plurality of frames obtained by the scan.

The instruction control unit 28 specifies a direction to perform the scan by the ultrasound probe 2 with respect to the current position of the ultrasound probe 2 on the basis of the current positional information of the ultrasound probe 2 acquired by the position sensor 14 and the boundary between the normal portion N and the abnormal portion J of the subject recognized by the boundary recognition unit 27.

The instruction control unit 28 instructs the user on the specified direction to perform the scan, by using the LED lamp 15 of the ultrasound probe 2. In this case, the instruction control unit 28 generates instruction information representing the instruction to the user, and wirelessly transmits the generated instruction information to the probe-side wireless communication unit 13 of the ultrasound probe 2 via the main body-side wireless communication unit 21. The instruction information received by the probe-side wireless communication unit 13 is sent to the LED lamp 15, and the LED lamp 15 blinks according to the instruction information.

For example, it is considered that, after the ultrasound probe 2 performs a scan to traverse the abnormal portion J along the first direction D1 as in the trajectory C1 indicated by the dotted line region in FIG. 9, the ultrasound probe 2 performs a scan along a second direction D2 orthogonal to the first direction D1. In this case, the instruction control unit 28 specifies a direction to pass the boundary B1 or B2 of the abnormal portion J recognized in the first scan, as the direction to perform the scan by the ultrasound probe 2 in the second scan.

Figure 10:
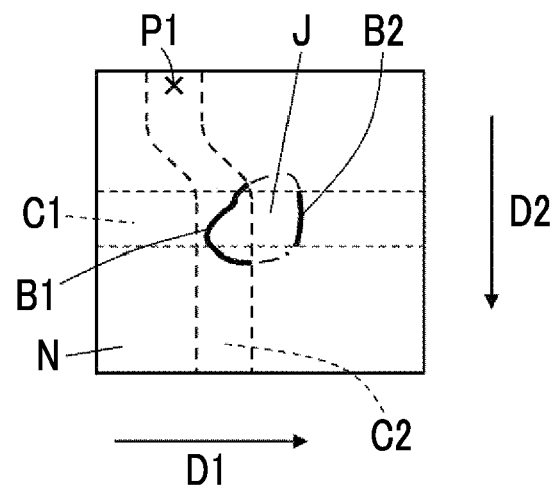
FIG. 10 is a diagram schematically illustrating a trajectory of two scans of the ultrasound probe with respect to the abnormal portion.

For example, as illustrated in FIG. 10, in the second scan, in a case where the ultrasound probe 2 performs the scan to progress along the second direction D2 from a state where the ultrasound probe 2 is arranged at a position P1, the instruction control unit 28 specifies a left direction with the progress direction of the ultrasound probe 2 as the front, as the direction to perform the scan so that the ultrasound probe 2 passes through the boundary B1. In this case, the instruction control unit 28 generates instruction information representing the scan of the ultrasound probe 2 in the left direction, and transmits the generated instruction information to the LED lamp 15 via the main body-side wireless communication unit 21 and the probe-side wireless communication unit 13 of the ultrasound probe 2.

In this manner, for example, the instruction control unit 28 instructs the user on the direction to perform the scan by the ultrasound probe 2 by turning on the right lamp 15A positioned on the left side with the progress direction of the ultrasound probe 2 as the front, among the right lamp 15A and the left lamp 15B of the LED lamp 15 as illustrated in FIG. 3. The user can perform the scan of the ultrasound probe 2 along, for example, a trajectory C2 illustrated in FIG. 10 by moving the ultrasound probe 2 according to the blinking of the LED lamp 15 without changing the orientation of the ultrasound probe 2.

The main body control unit 29 controls each unit of the diagnostic apparatus main body 3 on the basis of a control program and the like stored in advance.

The input device 30 is for the user to perform an input operation, and can be configured to comprise a keyboard, a mouse, a trackball, a touchpad, a touch panel, and the like.

The display control unit 23 performs predetermined processing on the ultrasound image or the like generated by the image generation unit 22, and displays the ultrasound image or the like on the monitor 24, under the control of the main body control unit 29.

The monitor 24 performs various kinds of display under the control of the display control unit 23. The monitor 24 includes a display device such as a liquid crystal display (LCD), or an organic electroluminescence (EL) display.

The main body-side processor 31 having the image generation unit 22, the display control unit 23, the memory control unit 26, the boundary recognition unit 27, the instruction control unit 28, and the main body control unit 29 is configured by a central processing unit (CPU) and a control program for causing the CPU to execute various kinds of processing, but the main body-side processor 31 may be configured by using a field programmable gate array (FPGA), a digital signal processor (DSP), an application specific integrated circuit (ASIC), a graphics processing unit (GPU), or other integrated circuits (IC) or may be configured by a combination thereof.

In addition, the image generation unit 22, the display control unit 23, the memory control unit 26, the boundary recognition unit 27, the instruction control unit 28, and the main body control unit 29 of the main body-side processor 31 can also be configured by being integrated partially or entirely into one CPU or the like.

Figure 11:
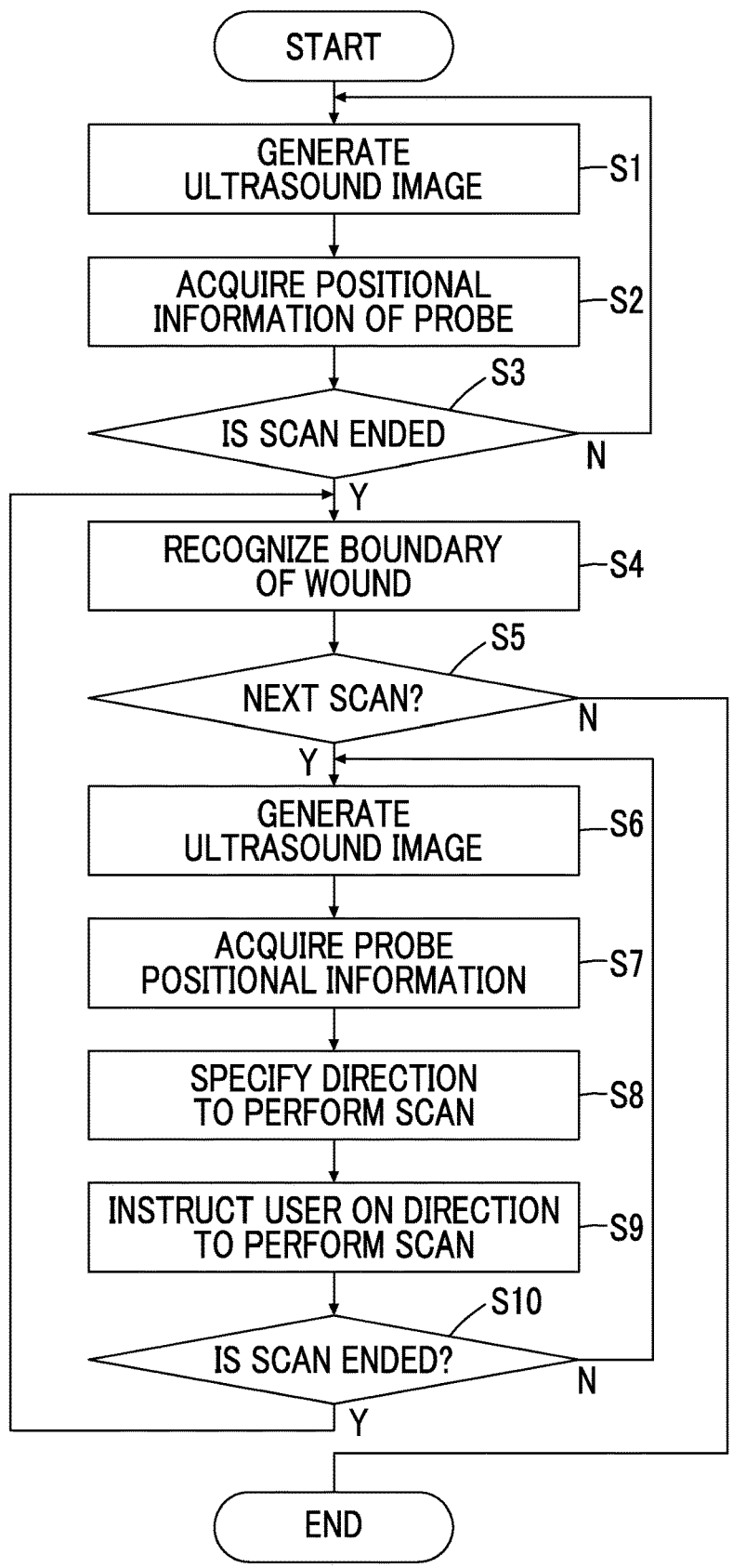
FIG. 11 is a flowchart illustrating an operation of the ultrasound diagnostic apparatus according to the first embodiment.

In the following, the basic operation of the ultrasound diagnostic apparatus 1 of the first embodiment will be described in detail using the flowchart illustrated in FIG. 11.

First, in Step S1, in order to capture the ultrasound image of the abnormal portion J, the ultrasound probe 2 is arranged on the body surface of the subject by the user. From this state, the ultrasound image is captured by the ultrasound probe 2 being moved along the first direction D1 as illustrated in FIG. 9.

In this case, an ultrasound beam is transmitted into the subject from the plurality of transducers of the transducer array 11 according to the drive signal from the pulser 32 of the transmission and reception circuit 12, the reception signal is output to amplification unit 33 of the transmission and reception circuit 12 from each transducer which has received the ultrasound echo from the subject.

The reception signal is amplified in the amplification unit 33, is subjected to the AD conversion in the AD conversion unit 34, and is phased and added in the beam former 35, and thereby the sound ray signal is generated. The sound ray signal is wirelessly transmitted from the probe-side wireless communication unit 13 to the main body-side wireless communication unit 21, and is sent to the image generation unit 22. The sound ray signal is subjected to the envelope detection processing by the signal processing unit 36 of the image generation unit 22 to be the B-mode image signal, and is output to the display control unit 23 via the DSC 37 and the image processing unit 38, and the ultrasound image is displayed on the monitor 24 under the control of the display control unit 23.

The ultrasound image generated in this manner is stored in the memory 25 via the memory control unit 26.

Next, in Step S2, the position sensor 14 acquires the positional information of the ultrasound probe 2. The memory control unit 26 stores the acquired positional information in the memory 25 in association with the ultrasound image generated in Step S1.

In subsequent Step S3, it is determined whether or not the scan of the ultrasound probe 2 along the first direction D1 illustrated in FIG. 9 is ended. For example, although not illustrated, in a case where an instruction to end the scan is input by the user via the input device 30, it is determined that the scan of the ultrasound probe 2 is ended, and an instruction to end the scan is not input, it is determined that the scan of the ultrasound probe 2 is continued.

In a case where it is determined in Step S3 that the scan of the ultrasound probe 2 along the first direction D1 is continued instead of being ended, the processing returns to Step S1, the ultrasound image is newly generated, the ultrasound image is stored in the memory 25, the positional information of the ultrasound probe 2 is newly acquired in subsequent Step S2, and the positional information is stored in the memory 25 in association with the ultrasound image generated in previous Step S1. In this manner, processing of Step S1 to Step S3 is repeated as long as it is determined in Step S3 that the scan of the ultrasound probe 2 is continued.

In a case where it is determined in Step S3 that the scan of the ultrasound probe 2 along the first direction D1 is ended, the processing proceeds to Step S4.

In Step S4, the boundary recognition unit 27 recognizes the boundaries B1 and B2 between the normal portion N and the abnormal portion J of the subject as illustrated in FIG. 9 by analyzing the ultrasound images of the plurality of frames stored in the memory 25 obtained by repeating Step S1 to Step S3.

In subsequent Step S5, it is determined whether or not the next scan, that is, the second scan of the ultrasound probe 2 is performed. For example, in a case where an instruction to perform the next scan is input by the user via the input device 30, it is determined that the next scan is performed, and an instruction not to perform the next scan is input, it is determined that the next scan is not performed.

In a case where it is determined in Step S5 that the next scan is performed, the processing proceeds to Step S6, and the second scan is started.

In Step S6, in order to perform the scan while moving the ultrasound probe 2 along the second direction D2, for example, as illustrated in FIG. 10, the user arranges the ultrasound probe 2 at the position P1 on the body surface of the subject. In this state, the ultrasound image is generated while the ultrasound probe 2 is moved. The generated ultrasound image is stored in the memory 25.

Next, in Step S7, the position sensor 14 acquires the positional information of the ultrasound probe 2. The memory control unit 26 stores the acquired positional information of the ultrasound probe 2 in the memory 25 in association with the ultrasound image generated in Step S6.

In subsequent Step S8, the instruction control unit 28 specifies the direction to perform the scan by the ultrasound probe 2 on the basis of the boundaries B1 and B2 between the normal portion N and the abnormal portion J of the subj etc recognized in Step S4, and the current positional information of the ultrasound probe 2 acquired in Step S7.

Here, it is considered that, in a case where the ultrasound probe 2 performs the scan along the second direction D2 different from the first direction D1 that is the direction of the first scan, by performing the scan of the ultrasound probe 2 to pass through the boundary B1 or B2 recognized in the first scan, the possibility of performing a scan to pass through the boundary not recognized in the first scan is increased. Therefore, the instruction control unit 28 specifies the left direction with the second direction D2, which is the progress direction of the ultrasound probe 2, as the front, as the direction to perform the scan by the ultrasound probe 2 so that the ultrasound probe 2 passes through the boundary B1 closer to the current position P1 of the ultrasound probe 2 among two boundaries B1 and B2 recognized in the first scan.

Next, in Step S9, the instruction control unit 28 instructs the user on the specified direction to perform the scan by blinking the LED lamp 15 attached to the ultrasound probe 2. Since the left direction with the progress direction of the ultrasound probe 2 as the front is specified as the direction to perform the scan, the instruction control unit 28 generates the instruction information for moving the ultrasound probe 2 in the left direction, and transmits the generated instruction information to the probe-side wireless communication unit 13 of the ultrasound probe 2 via the main body-side wireless communication unit 21. The instruction information transmitted to the probe-side wireless communication unit 13 is sent to the LED lamp 15.

In this manner, for example, the instruction control unit 28 instructs the user on the direction to perform the scan by the ultrasound probe 2 by turning on the right lamp 15A positioned on the left side with the progress direction of the ultrasound probe 2 as the front, among the right lamp 15A and the left lamp 15B of the LED lamp 15 as illustrated in FIG. 3. The user can perform the scan of the ultrasound probe 2 to pass the boundary B1 recognized in Step S4 along, for example, the trajectory C2 illustrated in FIG. 10 by moving the ultrasound probe 2 according to the blinking of the LED lamp 15 without changing the orientation of the ultrasound probe 2.

In this manner, the user can perform the scan of the ultrasound probe 2 to pass through the boundary B1, it is possible to improve the efficiency of the scan of the abnormal portion J by reliably scanning a non-scanned region of the abnormal portion J.

In Step S10, similarly to Step S3, it is determined whether or not the second scan is ended.

In a case where it is determined in Step S10 that the second scan is continued without being ended, the processing returns to Step S6. The ultrasound image is newly generated in Step S6, the ultrasound image is stored in the memory 25, the positional information of the ultrasound probe 2 is newly acquired in subsequent Step S7, and the positional information is stored in the memory 25 in association with the ultrasound image generated in previous Step S6.

Further, in Step S8, the direction to perform the scan by the ultrasound probe 2 is newly specified on the basis of the boundaries B1 and B2 between the normal portion N and the abnormal portion J of the subject recognized in Step S4, and the current positional information of the ultrasound probe 2 newly acquired in Step S7.

In subsequent Step S9, the direction to perform the scan newly specified in Step S8 is instructed to the user using the LED lamp 15.

In this manner, processing of Step S6 to Step S10 is repeated as long as it is determined in Step S10 that the second scan is continued without being ended.

Step S6 to Step S10 are repeated, the ultrasound probe 2 is moved by the user, and in a case where it is specified in Step S8 that the progress direction of the ultrasound probe 2, that is, the second direction D2 is the direction to perform the scan, the instruction control unit 28 can instruct the user that the direction to perform the scan is the second direction D2 by turning off all the right lamp 15A and the left lamp 15B of the LED lamp 15 or turning on all the right lamp 15A and the left lamp 15B in Step S9, for example.

In a case where it is determined in Step S10 that the second scan is ended, the processing returns to Step S4.

In Step S4, the boundary recognition unit 27 recognizes the boundary between the normal portion N and the abnormal portion J, which is positioned on the trajectory C2 illustrated in FIG. 10 by analyzing the ultrasound images of the plurality of frames stored in the memory 25 obtained by repeating Step S6 to Step S10.

In subsequent Step S5, it is determined whether or not the next scan, that is, the third scan is performed. In a case where it is determined in Step S5 that the next scan is performed, the processing proceeds to Step S6, and the third scan is started.

Figure 12:
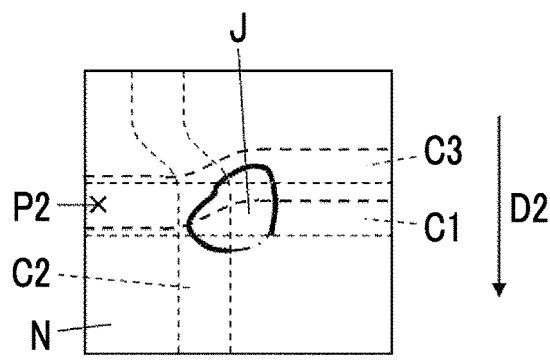
FIG. 12 is a diagram schematically illustrating a trajectory of three scans of the ultrasound probe with respect to the abnormal portion.

In Step S6, in order to perform the scan while moving the ultrasound probe 2 along the first direction D1, for example, as illustrated in FIG. 12, the user arranges the ultrasound probe 2 at a position P2 on the body surface of the subject. In this state, the ultrasound image is generated while the ultrasound probe 2 is moved. The generated ultrasound image is stored in the memory 25.

In Step S7, the position sensor 14 acquires the current positional information of the ultrasound probe 2. The acquired positional information is stored in the memory 25 in association with the ultrasound image generated in Step S6.

In Step S8, the instruction control unit 28 specifies the direction to perform the scan by the ultrasound probe 2 on the basis of the boundaries between the normal portion N and the abnormal portion J, the boundaries being respectively recognized in Step S4 after the end of the first scan and after the end of the second scan, and the current positional information of the ultrasound probe 2 acquired in previous Step S7.

Here, the current position P2 of the ultrasound probe 2 is near the position where the ultrasound probe 2 is arranged at the time of the start of the first scan, and in a case where the scan is performed straight from the position P2 along the first direction D1, the scan is performed on the trajectory substantially the same as the trajectory C1 of the first scan, which is inefficient as an examination. Therefore, the instruction control unit 28 specifies a scanning direction that reduces the overlapping with the trajectory C1 of the first scan, as the direction to perform the scan by the ultrasound probe 2. In the example of FIG. 12, the instruction control unit 28 specifies, as the direction to perform the scan, the left direction with the first direction D1, which is the progress direction of the ultrasound probe 2, as the front.

In subsequent Step S9, the instruction control unit 28 instructs the user on the direction to perform the scan specified in Step S8, that is, the left direction with the first direction D1, which is the progress direction of the ultrasound probe 2, as the front by blinking the LED lamp 15.

In this manner, the user can perform the scan of the ultrasound probe 2 along, for example, a trajectory C3 illustrated in FIG. 12 by moving the ultrasound probe 2 according to the blinking of the LED lamp 15 without changing the orientation of the ultrasound probe 2.

In this manner, since the user can perform the scan of the ultrasound probe 2 such that the overlapping with the trajectory C1 where the scan has been performed is reduced, it is possible to prevent the site where the scan has been performed from being repeatedly scanned, and to improve the efficiency of the examination while the abnormal portion J is sufficiently scanned.

In a case where the processing of Step S9 is completed, the processing proceeds to Step S10, and it is determined whether or not the third scan is ended. In a case where it is determined in Step S10 that the third scan is continued without being ended, the processing returns to Step S6. In this manner, Step S6 to Step S10 are repeated as long as it is determined in Step S10 that the third scan is continued without being ended.

In a case where it is determined in Step S10 that the third scan is ended, the processing returns to Step S4.

In Step S4, the boundary recognition unit 27 recognizes the boundary between the normal portion N and the abnormal portion J, which is positioned on the trajectory C3 illustrated in FIG. 12 by analyzing the ultrasound images of the plurality of frames stored in the memory 25 obtained by repeating Step S6 to Step S10 in the third scan.

In subsequent Step S5, it is determined whether or not the next scan, that is, the fourth scan is performed. In a case where it is determined in Step S5 that the next scan is performed, the processing proceeds to Step S6, and the fourth scan is started.

Figure 13:
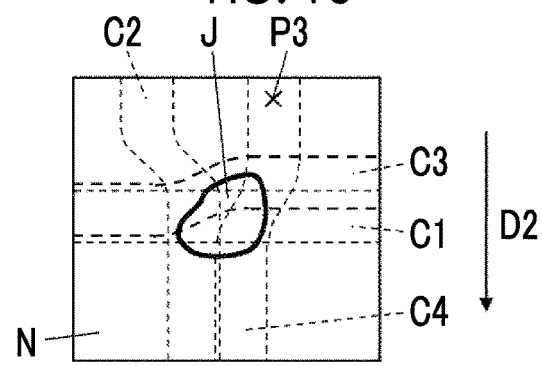
FIG. 13 is a diagram schematically illustrating a trajectory of four scans of the ultrasound probe with respect to the abnormal portion.

In Step S6, in order to perform the scan while moving the ultrasound probe 2 along the second direction D2, for example, as illustrated in FIG. 13, the user arranges the ultrasound probe 2 at a position P3 on the body surface of the subject. In this state, the ultrasound image is generated while the ultrasound probe 2 is moved. The generated ultrasound image is stored in the memory 25.

In Step S7, the position sensor 14 acquires the current positional information of the ultrasound probe 2. The acquired positional information is stored in the memory 25 in association with the ultrasound image generated in Step S6.

In Step S8, the instruction control unit 28 specifies the scanning direction passing through the boundary between the normal portion N and the abnormal portion J which has already been recognized, as the direction to perform the scan by the ultrasound probe 2 on the basis of the boundaries between the normal portion N and the abnormal portion J, the boundaries being respectively recognized in Step S4 after the end of the first to third scans, and the current positional information of the ultrasound probe 2 acquired in previous Step S7.

In the example of FIG. 13, the instruction control unit 28 specifies, as the direction to perform the scan, the right direction with the progress direction of the ultrasound probe 2, that is, the second direction D2, as the front.

In subsequent Step S9, the instruction control unit 28 instructs the user on the direction to perform the scan specified in Step S8, that is, the right direction with the second direction D2, which is the progress direction of the ultrasound probe 2, as the front by blinking the LED lamp 15. For example, the instruction control unit 28 instructs the user to move the ultrasound probe 2 in the right direction by turning on the left lamp 15B positioned on the right side with the progress direction of the ultrasound probe 2 as the front, among the right lamp 15A and the left lamp 15B illustrated in FIG. 3.

In this manner, the user can perform the scan of the ultrasound probe 2 along, for example, a trajectory C4 illustrated in FIG. 13 by moving the ultrasound probe 2 according to the blinking of the LED lamp 15 without changing the orientation of the ultrasound probe 2.

In a case where the processing of Step S9 is completed, the processing proceeds to Step S10, and it is determined whether or not the fourth scan is ended. In a case where it is determined in Step S10 that the fourth scan is continued without being ended, the processing returns to Step S6. In this manner, Step S6 to Step S10 are repeated as long as it is determined in Step S10 that the fourth scan is continued without being ended.

In a case where it is determined in Step S10 that the fourth scan is ended, the processing returns to Step S4.

In Step S4, the boundary recognition unit 27 recognizes the boundary between the normal portion N and the abnormal portion J, which is positioned on the trajectory C4 illustrated in FIG. 13 by analyzing the ultrasound images of the plurality of frames stored in the memory 25 obtained by repeating Step S6 to Step S10 in the fourth scan.

In subsequent Step S5, it is determined whether or not the next scan, that is, the fifth scan is performed. In a case where it is determined in Step S5 that the next scan is performed, the processing proceeds to Step S6, and the fifth scan is started.

In a case where an instruction not to perform the next scan is input by the user via the input device 30 by the user determining that the examination of the abnormal portion J is sufficiently performed or the like, it is determined that the next scan is not performed. In this case, the operation of examining the abnormal portion J using the ultrasound diagnostic apparatus 1 is ended.

As described above, with the ultrasound diagnostic apparatus 1 of the first embodiment of the present invention, since the scanning direction of the ultrasound probe 2 by the user is guided to scan a non-scanned region of the abnormal portion J, it is possible to improve the efficiency of the examination even while the abnormal portion J is sufficiently scanned.

The image generation unit 22 is provided in the diagnostic apparatus main body 3 in the first embodiment, but may be provided in the ultrasound probe 2 instead of being provided in the diagnostic apparatus main body 3. In this case, the ultrasound image generated in the image generation unit 22 is wirelessly transmitted from the probe-side wireless communication unit 13 to the main body-side wireless communication unit 21, and is sent from the main body-side wireless communication unit 21 to the display control unit 23, the memory control unit 26, and the boundary recognition unit 27.

As the example of the LED lamp 15, it has been described that the LED lamp 15 includes the right lamp 15A and the left lamp 15B as illustrated in FIG. 3, but the configuration of the LED lamp 15 is not limited thereto.

Figure 14:
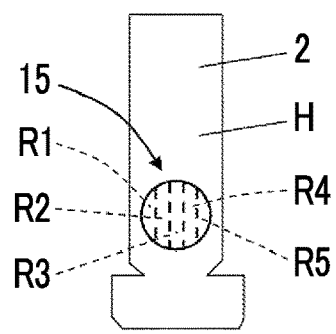
FIG. 14 is a diagram schematically illustrating another example of the LED lamp of the ultrasound probe in the first embodiment.
Figure 15:
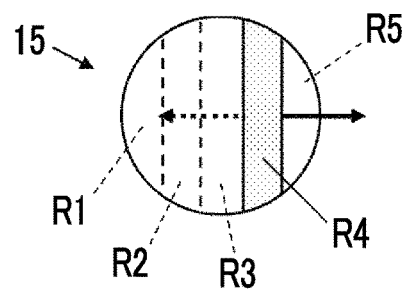
FIG. 15 is a diagram schematically illustrating an example of the turning on and off of the LED lamp.

For example, as illustrated in FIG. 14, the LED lamp 15 may be arranged on a side of the housing H on the progress direction side of the ultrasound probe 2, and may be configured by one light source having a plurality of light emitting regions R1 to R5 in the left and right direction with the progress direction of the ultrasound probe 2 as the front. In the example of FIG. 14, the LED lamp 15 has five light emitting regions R1 to R5. In this case, for example, as illustrated in FIG. 15, the instruction control unit 28 can instruct the user on the direction to perform the scan by causing the five light emitting regions R1 to R5 to emit light one by one along the right direction or the left direction with the progress direction of the ultrasound probe 2 as the front.

The method of instructing the user on the direction to perform the scan is not limited to the blinking of the LED lamp 15. For example, the LED lamp 15 can be configured by light sources of a plurality of colors, and the instruction control unit 28 can instruct the user on the direction to perform the scan by changing the color of light emitted from the LED lamp 15.

The scan of the ultrasound probe 2 along the first direction D1 and the scan of the ultrasound probe 2 along the second direction D2 are alternately performed, but the scanning method of the ultrasound probe 2 is not particularly limited thereto. For example, after the scan along the first direction D1 is ended, the scan along the first direction D1 may be performed as the next scan, and after the scan along the second direction D2 is ended, the scan along the second direction D2 may be performed as the next scan.

In the first scan of the ultrasound probe 2 along the first direction D1, in a case where both the boundaries B1 and B2 on both sides of the abnormal portion J are recognized by the boundary recognition unit 27 as illustrated in FIG. 9, the instruction control unit 28 can instruct the user to shift to the scan along the second direction D2 by turning on and off the LED lamp 15 for a certain period of time. Thus, in a case where the scan of the ultrasound probe 2 is performed along a certain direction and the boundaries on both sides of the abnormal portion J are recognized, it is possible for the user to easily understand the entire image of the abnormal portion J including a non-scanned portion of the abnormal portion J, and to examine the abnormal portion J more efficiently by shifting to the scan along a direction orthogonal to the certain direction.

Further, the instruction control unit 28 can estimate the remaining boundary, that is, the non-scanned boundary between the normal portion N and the abnormal portion J of the subject on the basis of the boundary recognized by the boundary recognition unit 27, and specify the direction to perform the scan on the basis of the estimated remaining boundary. In this case, for example, the instruction control unit 28 can specify a direction in which the ultrasound probe 2 approaches the estimated remaining boundary, as the direction to perform the scan. In this manner, since the ultrasound probe 2 is guided to the non-scanned region of the abnormal portion J, it is possible to improve the efficiency of the examination even while the abnormal portion J is sufficiently scanned.

In a case where a gap is generated between the current position of the ultrasound probe 2 and the scanned region, the instruction control unit 28 can specify the scanning direction in which the ultrasound probe 2 approaches the scanned region, as the direction to perform the scan on the basis of the positional information of the ultrasound probe 2 acquired by the position sensor 14. In this manner, since the generation of a non-scanned region is prevented, it is possible to efficiently scan the abnormal portion J without omission.

The ultrasound image is generated in Step S1, and the positional information of the ultrasound probe 2 is acquired in Step S2. However, as long as the ultrasound image and the positional information of the ultrasound probe 2 are stored in the memory 25 in association with each other, Step S1 may be performed after Step S2 is performed, or Step S1 and Step S2 may be performed in parallel.

For example, in a case where all the boundaries of the abnormal portion J are recognized by the boundary recognition unit 27, the instruction control unit 28 can notify the user of the recognition of the boundaries by using the LED lamp 15. In this case, for example, the instruction control unit 28 can notify the user by turning on and off the LED lamp 15 in a certain turning on-and-off pattern or the like. In this manner, since the user can understand that the abnormal portion J has been sufficiently scanned, it is possible to prevent the scan of the ultrasound probe 2 from being performed more than necessary, and to examine the abnormal portion J more efficiently.

Second Embodiment

In the first embodiment, the instruction control unit 28 instructs the user on the direction to perform the scan by the ultrasound probe 2, by using the LED lamp 15, but the method of instructing the direction to perform the scan is not limited thereto.

Figure 16:
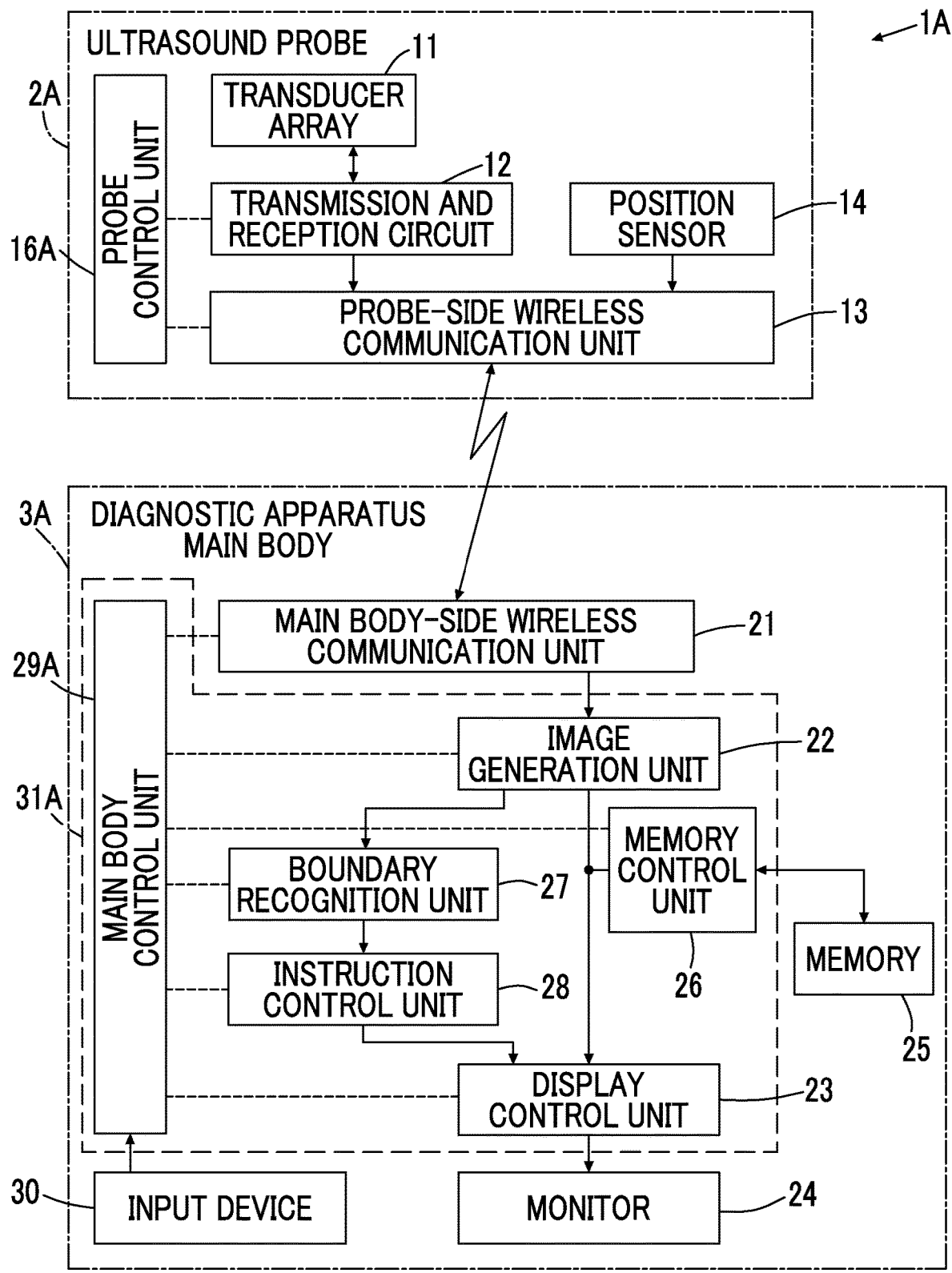
FIG. 16 is a block diagram illustrating a configuration of an ultrasound diagnostic apparatus according to a second embodiment.

FIG. 16 illustrates a configuration of an ultrasound diagnostic apparatus 1A according to a second embodiment. The ultrasound diagnostic apparatus 1A includes an ultrasound probe 2A and a diagnostic apparatus main body 3A.

The ultrasound probe 2A is obtained by excluding the LED lamp 15 and using a probe control unit 16A instead of the probe control unit 16, in the ultrasound probe 2 in the first embodiment illustrated in FIG. 1.

The diagnostic apparatus main body 3A is obtained by comprising a main body control unit 29A instead of the main body control unit 29, and connecting the instruction control unit 28 to the display control unit 23 instead of being connected to the main body-side wireless communication unit 21, in the diagnostic apparatus main body 3 in the first embodiment.

In the ultrasound diagnostic apparatus 1A, as the scanning direction instruction unit for instructing the user on the direction to perform the scan by the ultrasound probe 2, the monitor 24 of the diagnostic apparatus main body 3A is used.

Specifically, the instruction control unit 28 generates the instruction information for instructing the direction to perform the scan by the ultrasound probe 2A on the basis of the current positional information of the ultrasound probe 2A acquired by the position sensor 14 and the boundary between the normal portion N and the abnormal portion J of the subject recognized by the boundary recognition unit 27, and sends the generated instruction information to the display control unit 23. The display control unit 23 displays the direction to perform the scan on the monitor 24 according to the instruction information from the instruction control unit 28.

Figure 17:
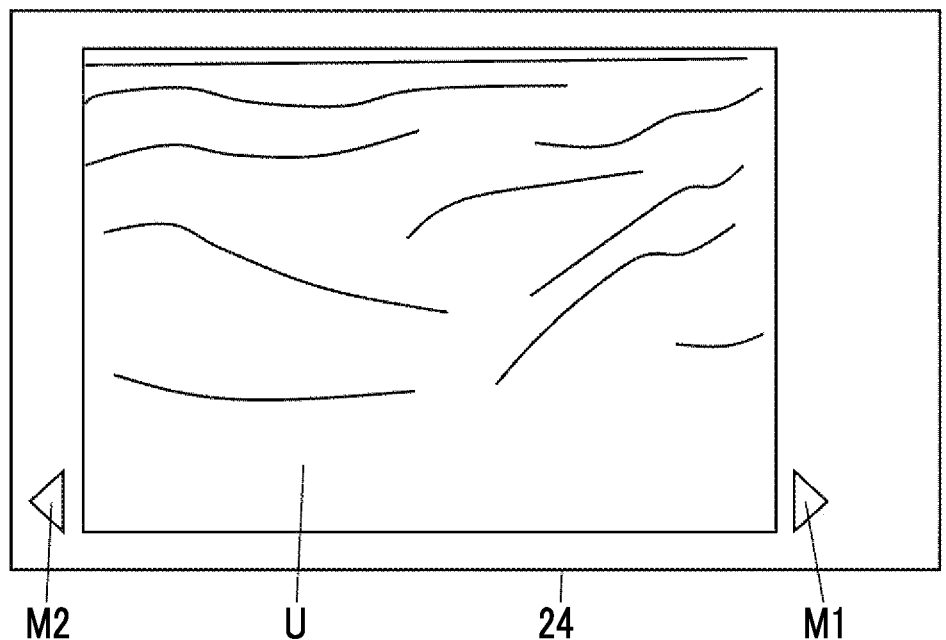
FIG. 17 is a diagram schematically illustrating an example of an instruction to a user, which is displayed on a monitor in the second embodiment.

In this case, the instruction control unit 28 displays a right side direction instruction mark M1 and a left side direction instruction mark M2 for instructing the user on the direction to perform the scan, together with an ultrasound image U displayed on the monitor 24, as illustrated in FIG. 17, for example. In this case, in a case where the direction to perform the scan is the left side with the progress direction of the ultrasound probe 2A as the front, the instruction control unit 28 displays the right side direction instruction mark M1 in an emphasized manner, and in a case where the direction to perform the scan is the right side with the progress direction of the ultrasound probe 2A as the front, the instruction control unit 28 displays the left side direction instruction mark M2 in an emphasized manner.

Here, displaying the right side direction instruction mark M1 or the left side direction instruction mark M2 in an emphasized manner means that the display mode of the right side direction instruction mark M1 or the left side direction instruction mark M2 is different from the normal display mode thereof, such as changing a display color of the right side direction instruction mark M1 or the left side direction instruction mark M2, and displaying the right side direction instruction mark M1 or the left side direction instruction mark M2 by turning on and off the right side direction instruction mark M1 or the left side direction instruction mark M2.

As described above, similarly to the case where the direction to perform the scan is instructed to the user by using the LED lamp 15 in the first embodiment, even in a case where the direction to perform the scan is instructed to the user by being displayed on the monitor 24, the scanning direction of the ultrasound probe 2A in the non-scanned region of the abnormal portion J is guided as the direction to perform the scan, and therefore, it is possible to sufficiently and efficiently examine the abnormal portion J.

Figure 18:
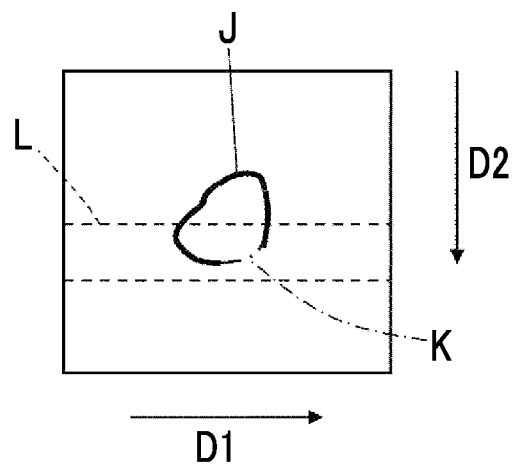
FIG. 18 is a diagram schematically illustrating a scanning line passing through a non-scanned portion in the abnormal portion.

As illustrated in FIG. 18, in a case where there is a non-scanned portion K such that the contour of the abnormal portion J is interrupted, the instruction control unit 28 can detect the non-scanned portion K on the basis of the boundary that has already been recognized by the boundary recognition unit 27, specify a scanning line L to perform the scan by ultrasound probe 2 to pass through the detected non-scanned portion K, and display the scanning line L on the monitor 24.

In this manner, it is possible to prevent omission of the examination of the abnormal portion J and to improve the efficiency of the examination.

Third Embodiment

The direction to perform the scan by the ultrasound probe 2 can be instructed to the user by vibrating the ultrasound probe 2, for example.

Figure 19:
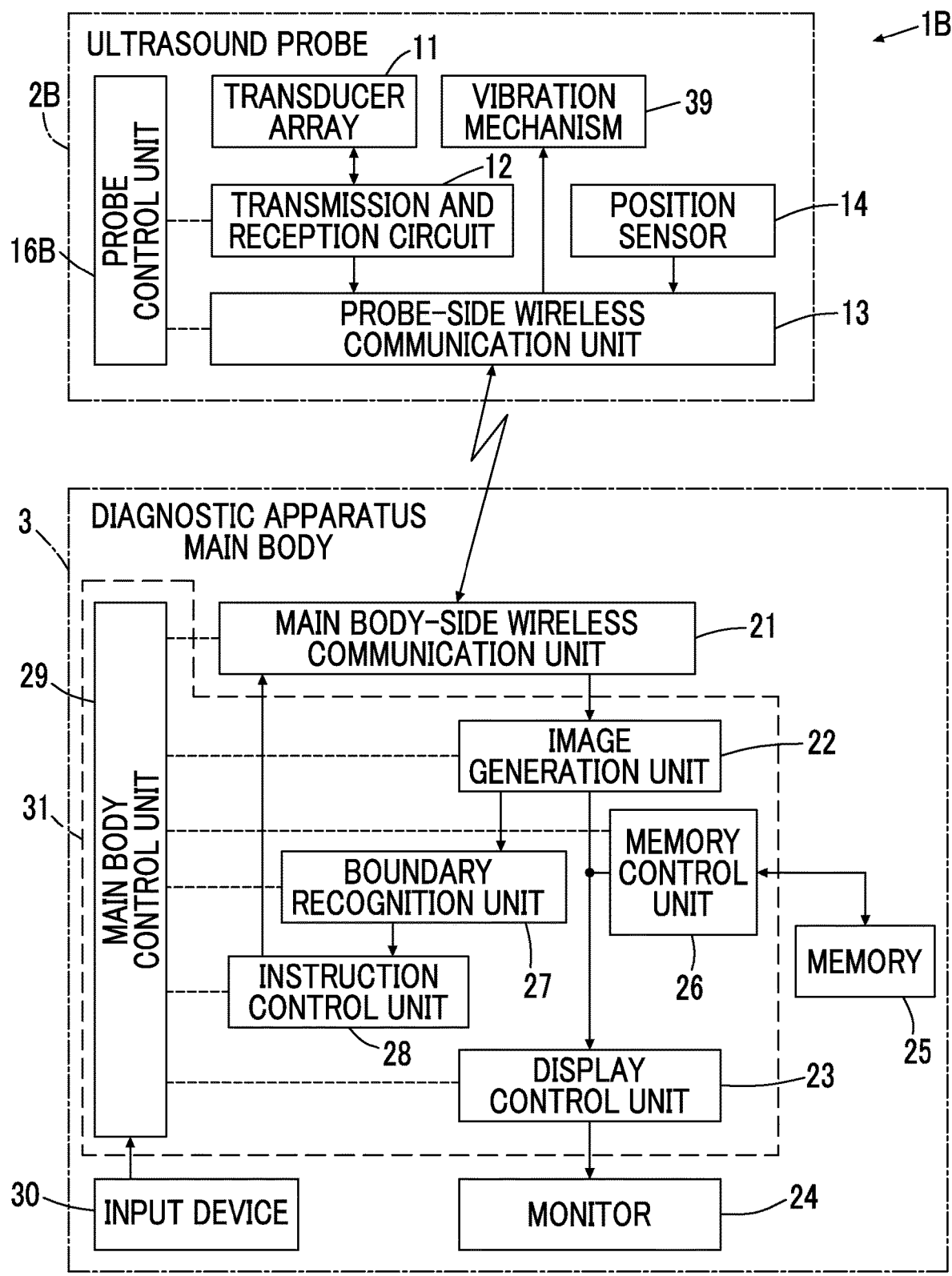
FIG. 19 is a block diagram illustrating a configuration of an ultrasound diagnostic apparatus according to a third embodiment.

FIG. 19 illustrates a configuration of an ultrasound diagnostic apparatus 1B according to a third embodiment. The ultrasound diagnostic apparatus 1B is obtained by comprising an ultrasound probe 2B instead of the ultrasound probe 2 in the ultrasound diagnostic apparatus 1 of the first embodiment illustrated in FIG. 1.

Further, the ultrasound probe 2B is obtained by comprising a vibration mechanism 39 instead of the LED lamp 15 and comprising a probe control unit 16B instead of the probe control unit 16, in the ultrasound probe 2 in the first embodiment.

The vibration mechanism 39 is configured by a small so-called vibration motor or the like, and slightly vibrates the ultrasound probe 2B on the basis of the instruction information generated by the instruction control unit 28.

For example, the instruction control unit 28 can cause the vibration mechanism 39 to vibrate the ultrasound probe 2B once within a certain period of time in order to instruct the user to move the ultrasound probe 2B in the left direction with the progress direction of the ultrasound probe 2B as the front, and cause the vibration mechanism 39 to vibrate the ultrasound probe 2B twice in succession within a period of time in order to instruct the user to move the ultrasound probe 2B in the right direction with the progress direction of the ultrasound probe 2B as the front. Thus, the instruction control unit 28 can instruct the user on the direction to perform the scan by vibrating the ultrasound probe 2B in a vibration pattern predetermined according to the direction to perform the scan.

As described above, similarly to the case where the direction to perform the scan is instructed to the user by using the LED lamp 15 in the first embodiment, even in a case where the direction to perform the scan is instructed to the user by vibrating the ultrasound probe 2B, the scanning direction of the ultrasound probe 2B in the non-scanned region of the abnormal portion J is guided as the direction to perform the scan, and therefore, it is possible to sufficiently and efficiently examine the abnormal portion J.

Note that it is possible to instruct the user on the direction to perform the scan by vibrating the diagnostic apparatus main body 3 instead of vibrating the ultrasound probe 2B.

Figure 20:
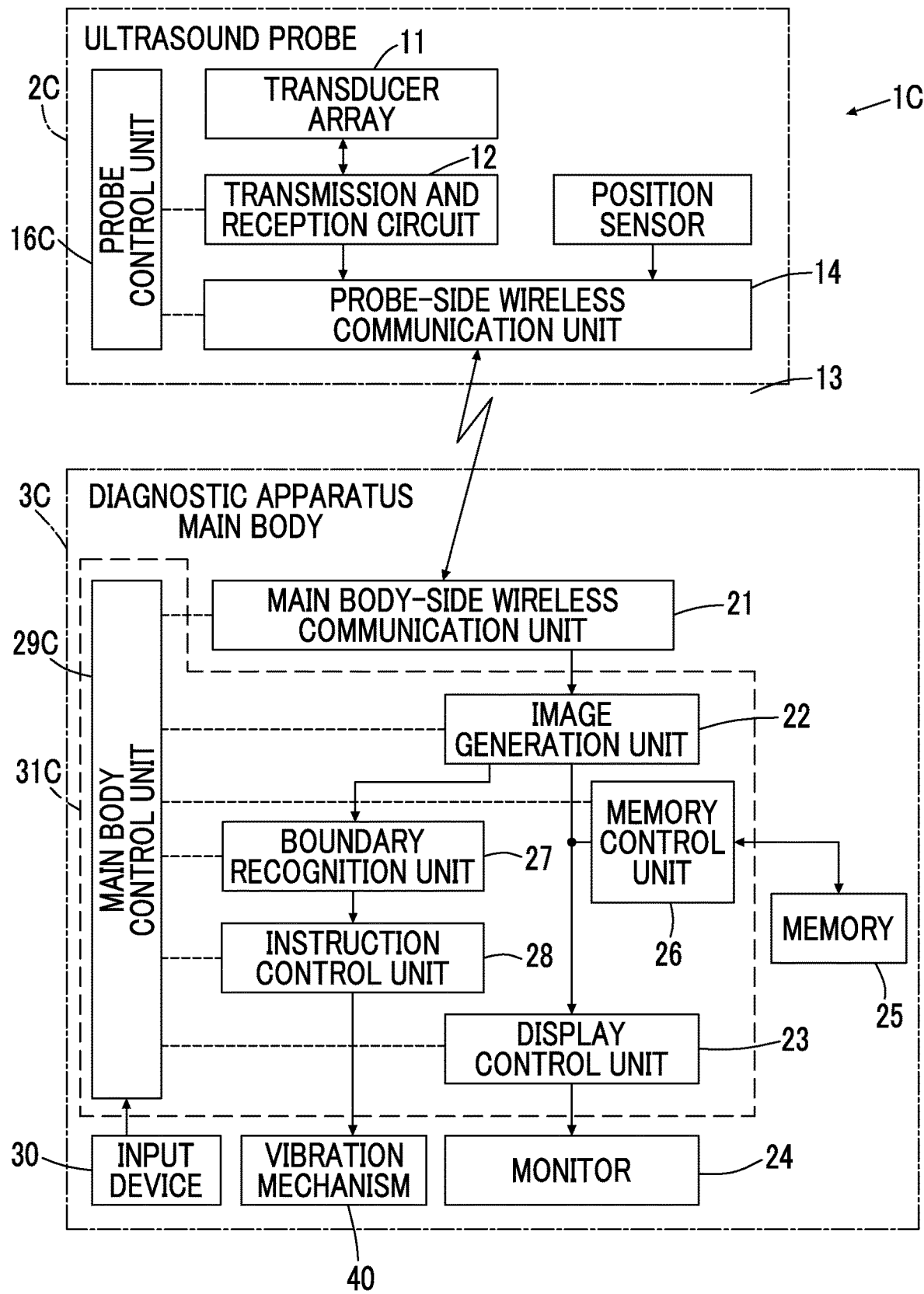
FIG. 20 is a block diagram illustrating a configuration of an ultrasound diagnostic apparatus according to a modification example of the third embodiment.

FIG. 20 illustrates a configuration of an ultrasound diagnostic apparatus 1C according to a modification example of the third embodiment. The ultrasound diagnostic apparatus 1C includes an ultrasound probe 2C and a diagnostic apparatus main body 3C.

The ultrasound probe 2C is obtained by excluding the LED lamp 15 and using a probe control unit 16C instead of the probe control unit 16, in the ultrasound probe 2 in the first embodiment illustrated in FIG. 1.

The diagnostic apparatus main body 3C is obtained by adding a vibration mechanism 40 and comprising a main body control unit 29C instead of the main body control unit 29, in the diagnostic apparatus main body 3 of the first embodiment. Further, instead of the main body-side processor 31, a main body-side processor 31C including the main body control unit 29C is configured. The instruction control unit 28 is connected to the vibration mechanism 40 instead of being connected to the main body-side wireless communication unit 21.

The vibration mechanism 40 is configured by a small so-called vibration motor or the like, and slightly vibrates the diagnostic apparatus main body 3C on the basis of the instruction information generated by the instruction control unit 28.

For example, the instruction control unit 28 can cause the vibration mechanism 40 to vibrate the diagnostic apparatus main body 3C once within a certain period of time in order to instruct the user to move the ultrasound probe 2B in the left direction with the progress direction of the ultrasound probe 2B as the front, and cause the vibration mechanism 40 to vibrate the diagnostic apparatus main body 3C twice in succession within a period of time in order to instruct the user to move the ultrasound probe 2B in the right direction with the progress direction of the ultrasound probe 2B as the front. Thus, the instruction control unit 28 can instruct the user on the direction to perform the scan by vibrating the diagnostic apparatus main body 3C in a vibration pattern predetermined according to the direction to perform the scan.

Although not illustrated, in addition to the vibration mechanism 40 provided in the diagnostic apparatus main body 3C, the vibration mechanism 39 may be provided in the ultrasound probe 2C. In this case, the instruction control unit 28 can vibrate any one of the ultrasound probe 2C or the diagnostic apparatus main body 3C according to the direction to perform the scan, for example.

The instruction control unit 28 can decide the correspondence relationship between the vibration of the ultrasound probe 2C or the diagnostic apparatus main body 3C and the direction to perform the scan according to device holding information representing whether the user holds the ultrasound probe 2C or the diagnostic apparatus main body 3C with the user's right hand or left hand, for example. The device holding information can be input by the user via the input device 30, for example.

For example, by providing a holding hand recognition unit (not illustrated) that recognizes whether the user holds the ultrasound probe 2C or the diagnostic apparatus main body 3C with the user's right hand or left hand to the ultrasound probe 2C or the diagnostic apparatus main body 3C by reading the user's fingerprint, the instruction control unit 28 can decide the correspondence relationship between the vibration of the ultrasound probe 2C or the diagnostic apparatus main body 3C and the direction to perform the scan on the basis of the recognition result of the holding hand recognition unit.

Fourth Embodiment

For example, a tomographic plane of the inside of the subject may not be depicted in the ultrasound image by the ultrasound probe 2 being separated from the body surface of the subject during the examination of the abnormal portion J. In this case, it is possible to prevent the omission of the examination by notifying the portion that is not depicted in the ultrasound image to the user.

Figure 21:
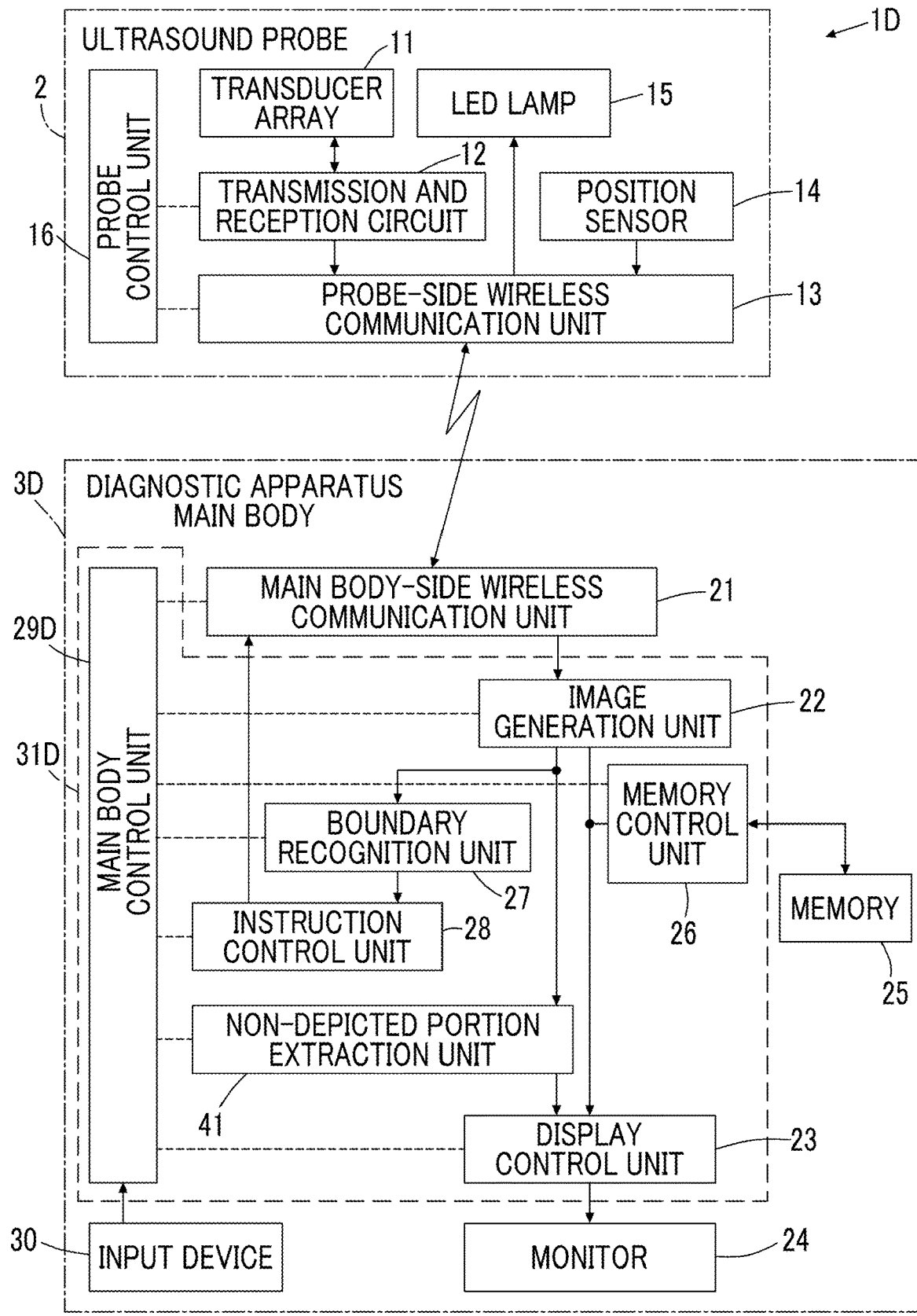
FIG. 21 is a block diagram illustrating a configuration of an ultrasound diagnostic apparatus according to a fourth embodiment.

FIG. 21 illustrates a configuration of an ultrasound diagnostic apparatus 1D according to a fourth embodiment. The ultrasound diagnostic apparatus 1D is obtained by comprising a diagnostic apparatus main body 3D instead of the diagnostic apparatus main body 3 in the ultrasound diagnostic apparatus 1 of the first embodiment illustrated in FIG. 1. Further, instead of the main body-side processor 31, a main body-side processor 31D including a main body control unit 29D and a non-depicted portion extraction unit 41 is configured.

The diagnostic apparatus main body 3D is obtained by adding the non-depicted portion extraction unit 41 and comprising the main body control unit 29D instead of the main body control unit 29, in the diagnostic apparatus main body 3 in the first embodiment.

In the diagnostic apparatus main body 3D, the non-depicted portion extraction unit 41 is connected to the image generation unit 22, and the display control unit 23 is connected to the non-depicted portion extraction unit 41.

The non-depicted portion extraction unit 41 identifies a portion, which is not depicted in the ultrasound image U due to the separation of the ultrasound probe 2 from the body surface of the subject, on the basis of the ultrasound image U generated by the image generation unit 22 and the positional information of the ultrasound probe 2 acquired by the position sensor 14, and displays the identified portion on the monitor 24.

Figure 22:
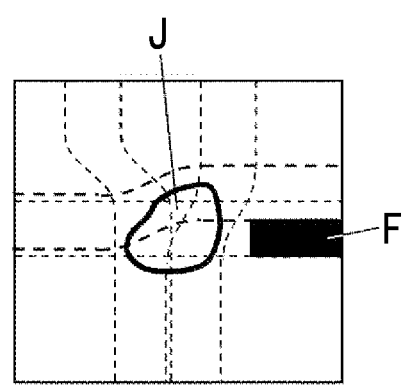
FIG. 22 is a diagram illustrating a display example of a non-depicted portion in the fourth embodiment.

In this case, the non-depicted portion extraction unit 41 can analyze the ultrasound images U of the plurality of frames generated by the image generation unit 22 to specify the ultrasound image U in which the tomographic plane of the inside of the subject is not depicted, and identify the portion of which the tomographic plane of the subject is not depicted in the ultrasound image U, among the regions on the body surface of the subject which have been already scanned, on the basis of the positional information of the ultrasound probe 2 corresponding to the ultrasound image U. Further, the non-depicted portion extraction unit 41 can display a non-depicted portion F of which the tomographic plane of the subject is not depicted in the ultrasound image U, on the monitor 24 by emphasizing the non-depicted portion F over the other portions, as illustrated in FIG. 22.

Thus, with the ultrasound diagnostic apparatus 1D according to the fourth embodiment, since the non-depicted portion F of which the tomographic plane of the subject is not depicted in the ultrasound image U is displayed on the monitor 24, it is possible for the user to understand the position of the non-depicted portion F, and for the user to determine whether or not rescanning of the position of the non-depicted portion F is necessary. Therefore, it is possible to improve the efficiency of the examination while preventing the omission of the examination of the abnormal portion J.

In a case where the non-depicted portion F displayed on the monitor 24 is selected by the user via the input device 30, the instruction control unit 28 can specify the direction to perform the scan by the ultrasound probe 2 to pass through the non-depicted portion F selected by the user. In this manner, it is possible to reliably scan the position of the non-depicted portion F, and to prevent the omission of the examination.

Fifth Embodiment

It is possible for the user to visually understand the region that has already been scanned, by displaying the trajectory of the scan of the ultrasound probe 2 by the user on the monitor 24.

Figure 23:
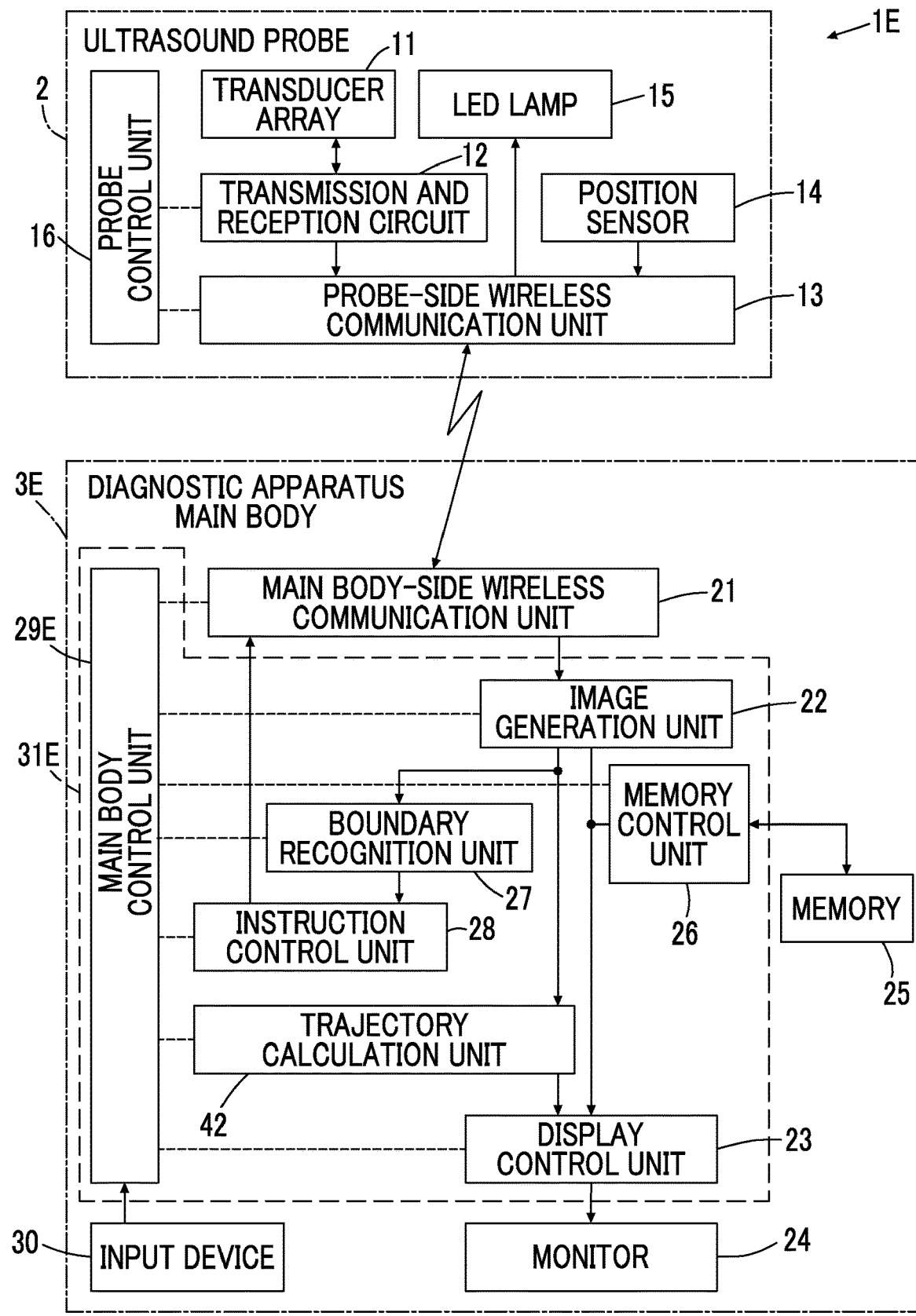
FIG. 23 is a block diagram illustrating a configuration of an ultrasound diagnostic apparatus according to a fifth embodiment.

FIG. 23 illustrates a configuration of an ultrasound diagnostic apparatus 1E according to a fifth embodiment. The ultrasound diagnostic apparatus 1E is obtained by comprising a diagnostic apparatus main body 3E instead of the diagnostic apparatus main body 3 in the ultrasound diagnostic apparatus 1 of the first embodiment illustrated in FIG. 1.

The diagnostic apparatus main body 3E is obtained by adding a trajectory calculation unit 42 and comprising a main body control unit 29E instead of the main body control unit 29, in the diagnostic apparatus main body 3 in the first embodiment. Further, instead of the main body-side processor 31, a main body-side processor 31E including the main body control unit 29E and the trajectory calculation unit 42 is configured. In the diagnostic apparatus main body 3E, the trajectory calculation unit 42 is connected to the image generation unit 22, and the display control unit 23 is connected to the trajectory calculation unit 42.

For example, the trajectory calculation unit 42 calculates trajectories C1 to C4 of the scan of the ultrasound probe 2 as illustrated in FIG. 13, and displays the calculated trajectories C1 to C4 on the monitor 24. In this manner, it is possible for the user to examine the abnormal portion J while easily understanding the region on the body surface of the subject which has been already scanned.

Further, in a case where any position on the trajectories C1 to C4 displayed on the monitor 24 is designated by the user via the input device 30, the main body control unit 29E controls the memory control unit 26 such that the ultrasound image U corresponding to the position designated by the user is read out from the memory 25 and is displayed on the monitor 24. It is possible for the user to proceed with the examination of the abnormal portion J while checking the ultrasound image U displayed on the monitor 24 in this manner.

As described above, with the ultrasound diagnostic apparatus 1E according to the fifth embodiment, the trajectories C1 to C4 of the scan of the ultrasound probe 2 are displayed on the monitor 24, and the ultrasound image U corresponding to the position on the trajectories C1 to C4 designated by the user is read out from the memory 25, and is displayed on the monitor 24. Therefore, it is possible for the user to efficiently perform the examination while easily understanding the status of the examination.

EXPLANATION OF REFERENCES 1, 1A, 1B, 1C, 1D, 1E: ultrasound diagnostic apparatus
2, 2A, 2B, 2C: ultrasound probe
3, 3A, 3C, 3D, 3E: diagnostic apparatus main body
11: transducer array
12: transmission and reception circuit
13: probe-side wireless communication unit
14: position sensor
15: LED lamp
15A: right lamp
15B: left lamp
16, 16A, 16B, 16C: probe control unit
21: main body-side wireless communication unit
22: image generation unit
23: display control unit
24: monitor
25: memory
26: memory control unit
27: boundary recognition unit
28: instruction control unit
29, 29A, 29C, 29D, 29E: main body control unit
30: input device
31, 31A, 31C, 31D, 31E: main body-side processor
32: pulser
33: amplification unit
34: AD conversion unit
35: beam former
36: signal processing unit
37: DSC
38: image processing unit
39, 40: vibration mechanism
41: non-depicted portion extraction unit
42: trajectory calculation unit
A1: unclear layered structure
A2: Cobblestone-like pattern
A3: Cloud-like pattern
A4: pattern
B1, B2: boundary
C1 to C4: trajectory
D1: first direction
D2: second direction
F: non-depicted portion
H: housing
J: abnormal portion
L: scanning line
M1: right side direction instruction mark
M2: left side direction instruction mark
N: normal portion
P1 to P3: position
R1 to R5: light emitting region
U: ultrasound image

What is claimed is:

1. An ultrasound diagnostic apparatus comprising:
an ultrasound probe;
a position sensing device that is attached to the ultrasound probe, and configured to acquire positional information of the ultrasound probe;
a scanning direction instructing device formed by a vibration mechanism that is included in the ultrasound probe, and configured to instruct a user on a direction to perform the scan by the ultrasound probe;
a processor configured to
generate an ultrasound image by performing a scan of an ultrasound beam on an abnormal portion of a subject by using the ultrasound probe,
recognize a boundary between a normal portion and the abnormal portion of the subject by analyzing the ultrasound image,
specify the direction to perform the scan by the ultrasound probe based on the positional information of the ultrasound probe acquired by the position sensing device and the boundary, and
instruct the user on the specified direction to perform the scan according to a vibration pattern of the vibration mechanism of the scanning direction instructing device.

2. An ultrasound diagnostic apparatus comprising:
an ultrasound probe;
a position sensing device that is attached to the ultrasound probe, and configured to acquire positional information of the ultrasound probe;
a tablet terminal connected to the ultrasound probe;
a scanning direction instructing device formed by a vibration mechanism that is included in the tablet terminal, and configured to instruct a user on a direction to perform the scan by the ultrasound probe; and
a processor configured to
generate an ultrasound image by performing a scan of an ultrasound beam on an abnormal portion of a subject by using the ultrasound probe, recognize a boundary between a normal portion and the abnormal portion of the subject by analyzing the ultrasound image, specify the direction to perform the scan by the ultrasound probe based on the positional information of the ultrasound probe acquired by the position sensing device and the boundary, and instruct the user on the specified direction to perform the scan according to a vibration pattern of the vibration mechanism.

3. The ultrasound diagnostic apparatus according to claim 1, wherein the processor is further configured to specify a scanning direction that reduces overlapping with a scanned region based on the positional information of the ultrasound probe acquired by the position sensing device.

4. The ultrasound diagnostic apparatus according to claim 2, wherein the processor is further configured to specify a scanning direction that reduces overlapping with a scanned region based on the positional information of the ultrasound probe acquired by the position sensing device.

5. An ultrasound diagnostic apparatus comprising:

an ultrasound probe;

a position sensing device that is attached to the ultrasound probe, and configured to acquire positional information of the ultrasound probe;

a scanning direction instructing device configured to instruct a user on a direction to perform the scan by the ultrasound probe; and a processor configured to generate an ultrasound image by performing a scan of an ultrasound beam on an abnormal portion of a subject by using the ultrasound probe, recognize a boundary between a normal portion and the abnormal portion of the subject by analyzing the ultrasound image, in a case where a gap is generated between the ultrasound probe and a scanned region, specify a scanning direction to approach the scanned region as the direction to perform the scan by the ultrasound probe, based on the positional information of the ultrasound probe acquired by the position sensing device, and instruct the user on the specified direction to perform the scan by using the scanning direction instructing device.

6. The ultrasound diagnostic apparatus according to claim 1, wherein in a case where a gap is generated between the ultrasound probe and a scanned region, the processor is further configured to specify a scanning direction to approach the scanned region based on the positional information of the ultrasound probe acquired by the position sensing device.

7. The ultrasound diagnostic apparatus according to claim 2, wherein in a case where a gap is generated between the ultrasound probe and a scanned region, the processor is further configured to specify a scanning direction to approach the scanned region based on the positional information of the ultrasound probe acquired by the position sensing device.

8. The ultrasound diagnostic apparatus according to claim 1, wherein the processor is further configured to specify a scanning direction passing through the boundary based on the positional information of the ultrasound probe acquired by the position sensing device.

9. An ultrasound diagnostic apparatus comprising:

a monitor;

an ultrasound probe;

a position sensing device that is attached to the ultrasound probe, and configured to acquire positional information of the ultrasound probe;

a scanning direction instructing device configured to instruct a user on a direction to perform the scan by the ultrasound probe; and a processor configured to generate an ultrasound image by performing a scan of an ultrasound beam on an abnormal portion of a subject by using the ultrasound probe, recognize a boundary between a normal portion and the abnormal portion of the subject by analyzing the ultrasound image, specify the direction to perform the scan by the ultrasound probe based on the positional information of the ultrasound probe acquired by the position sensing device and the boundary, instruct the user on the specified direction to perform the scan by using the scanning direction instructing device, identify a portion which is not depicted in the ultrasound image due to separation of the ultrasound probe from a body surface of the subject, based on the ultrasound image and the positional information of the ultrasound probe, and display the portion on the monitor.

10. An ultrasound diagnostic apparatus comprising:

an ultrasound probe;

a position sensing device that is attached to the ultrasound probe, and configured to acquire positional information of the ultrasound probe;

a scanning direction instructing device configured to instruct a user on a direction to perform the scan by the ultrasound probe; and a processor configured to generate an ultrasound image by performing a scan of an ultrasound beam on an abnormal portion of a subject by using the ultrasound probe, recognize a boundary between a normal portion and the abnormal portion of the subject by analyzing the ultrasound image, in a case where, while performing the scan on the abnormal portion in one direction of two directions orthogonal to each other, boundaries on both sides of the abnormal portion along the one direction are recognized, specify the other direction of the two directions as the direction to perform the scan by the ultrasound probe based on the positional information of the ultrasound probe acquired by the position sensing device, and instruct the user to shift to the scan in the direction to perform the scan by the ultrasound probe by using the scanning direction instructing device.

11. The ultrasound diagnostic apparatus according to claim 1, wherein the processor is further configured to estimate a remaining boundary between the normal portion and the abnormal portion of the subject based on the boundary, and specify the direction to perform the scan based on the estimated remaining boundary.

12. An ultrasound diagnostic apparatus comprising:

a monitor;

a memory;
an ultrasound probe;
a position sensing device that is attached to the ultrasound probe, and configured to acquire positional information of the ultrasound probe; and
a processor configured to
generate an ultrasound image by performing a scan of an ultrasound beam on an abnormal portion of a subject by using the ultrasound probe,
store the ultrasound image and the positional information of the ultrasound probe acquired by the position sensing device in association with each other, in the memory,
calculate a trajectory of the scan of the ultrasound probe,
display the trajectory on the monitor,
once any position on the trajectory displayed on the monitor is designated by a user,
   read out the ultrasound image corresponding to the any position from the memory, and
   display the ultrasound image corresponding to the any position on the monitor.

\* \* \* \* \*